United States Patent
Lu et al.

(10) Patent No.: US 9,993,440 B2
(45) Date of Patent: Jun. 12, 2018

(54) ENZYME RESPONSIVE NANOCAPSULES FOR PROTEIN DELIVERY

(75) Inventors: Yunfeng Lu, Culver City, CA (US); Tatiana Segura, Los Angeles, CA (US); Suwei Zhu, Los Angeles, CA (US); Jing Wen, Culver City, CA (US)

(73) Assignee: The Regents of the University of California, Oakland, CA (US)

( * ) Notice: Subject to any disclaimer, the term of this patent is extended or adjusted under 35 U.S.C. 154(b) by 297 days.

(21) Appl. No.: 14/342,524

(22) PCT Filed: Sep. 4, 2012

(86) PCT No.: PCT/US2012/053694
§ 371 (c)(1),
(2), (4) Date: Sep. 8, 2014

(87) PCT Pub. No.: WO2013/033717
PCT Pub. Date: Mar. 7, 2013

(65) Prior Publication Data
US 2015/0359752 A1    Dec. 17, 2015

Related U.S. Application Data

(60) Provisional application No. 61/530,661, filed on Sep. 2, 2011.

(51) Int. Cl.
*A61K 47/65* (2017.01)
*A61K 9/51* (2006.01)
*A61K 38/18* (2006.01)
*A61K 9/19* (2006.01)

(52) U.S. Cl.
CPC .............. *A61K 9/5169* (2013.01); *A61K 9/19* (2013.01); *A61K 9/5138* (2013.01); *A61K 9/5192* (2013.01); *A61K 38/1866* (2013.01); *A61K 47/65* (2017.08)

(58) Field of Classification Search
CPC ...... A61K 9/5169; A61K 9/19; A61K 9/5138; A61K 9/9152; A61K 38/1866; A61K 47/48338
See application file for complete search history.

(56) References Cited

U.S. PATENT DOCUMENTS

| 6,153,217 A | 11/2000 | Jin et al. |
| 2004/0116348 A1 | 6/2004 | Chau et al. |
| 2005/0119762 A1 | 6/2005 | Zilla et al. |
| 2009/0060894 A1 | 3/2009 | Somberg et al. |
| 2010/0010102 A1 | 1/2010 | Roy et al. |
| 2011/0318297 A1 | 12/2011 | Lu et al. |
| 2014/0037748 A1 | 2/2014 | Tang et al. |

FOREIGN PATENT DOCUMENTS

| WO | 2008073856 | 6/2008 | |
| WO | WO2008073856 | * 6/2008 | ............ A61K 48/00 |
| WO | 2010017215 | 2/2010 | |
| WO | 2013006762 | 1/2013 | |
| WO | 2013006763 | 1/2013 | |

OTHER PUBLICATIONS

Glangchai et al., JI. Controlled Rel. 125 (2008) 263-272.*
Gu et al., Protein Nanocapsule Weaved with Enzymatically Degradable Polymeric Network, Nano Lett., vol. 9, No. 12, 2009.*
Kim and Healy, Synthesis and Characterization of Injectable Poly(N-isopropylacrylamide-co-acrylic acid) Hydrogels with Proteolytically Degradable Cross-Links, Biomacromolecules 2003, 4, 1214-1223.*
Yan et al., Nature Nanotechnology, vol. 5, Jan. 2010, 48-53.*
Tokatlian et al., Biomaterials 31 (2010) 8072-8080.*
Werle and Bernkop-SChnurch, Strategies to improve plasma half life time of peptide and protein drugs, Amino Acids (2006) 30: 351-367.*
Gu et al., Protein Nanocapsule Weaved with Enzymatically Degradable Polymeric Network, Nano Lett., vol. 9, No. 12, pp. 4533-4538, 2009.*
PCT International Search Report and Written Opinion dated Dec. 14, 2012, for PCT Application No. PCT/US2012/053694.
Wen, J., et al., "Controlled Protein Delivery Based on Enzyme-Responsive Nanocapsules", Advanced Materials, 2011, pp. 4549-4553, vol. 23, Issue No. 39.
Leader et al., "Protein therapeutics: a summary and pharmacological classification," Nat. Rev. Drug Discovery, 2008, 7(1): 21-39.
Hu et al., "Cytosolic delivery of membrane-impermeable molecules in dendritic cells using pH-responsive core-shell nanoparticles", Nano Lett., 2007, 7(10): 3056-3064.
Hu et al., "Cytosolic delivery mediated via electrostatic surface binding of protein, virus, or siRNA cargos to pH-responsive core-shell gel particles", Biomacromolecules, 2009, 10(4): 756-765.
Kataoka et al., "Totally synthetic polymer gels responding to external glucose concentration: their preparation and application to on-off regulation of insulin release", J. Am. Chem. Soc., 1998, 120(48): 12694-12695.

(Continued)

Primary Examiner — Karlheinz R. Skowronek
Assistant Examiner — Joseph Fischer
(74) Attorney, Agent, or Firm — Gates & Cooper LLP

(57) ABSTRACT

The invention provides methods of making and using compositions comprising a polymer shell designed to deliver polypeptides to selected environments. In embodiments of the invention, different environmental conditions are harnessed to allow the selective degradation of the polymer shell and the consequential release of one or polypeptides encapsulated therein. In illustrative embodiments, polymer components of the shell are interconnected by peptide-containing crosslinker moieties, linkages which maintain the integrity of the polymer shell under certain environmental conditions, but can also be cleaved when combined with a selected protease.

12 Claims, 24 Drawing Sheets

(56) References Cited

OTHER PUBLICATIONS

Aimetti et al., "Poly (ethylene glycol) hydrogels formed by thiol-ene photopolymerization for enzyme-responsive protein delivery", Biomaterials, 2009, 30(30): 6048-6054.

Franssen et al., "Controlled release of a model protein from enzymatically degrading dextran microspheres", J. Controlled Release, 1999, 59(2): 219-228.

Tessmar et al., "Matrices and scaffolds for protein delivery in tissue engineering", Adv. Drug Delivery Rev., 2007, 59(4): 274-291.

Lei et al., "Hyaluronic acid and fibrin hydrogels with concentrated DNA/PEI polyplexes for local gene delivery", J. Control. Release, 2011, 153(3): 255-261.

Moon et al., "Biomimetic hydrogels with pro-angiogenic properties", Biomaterials, 2010, 31(14): 3840-3847.

Phelps et al., "Bioartificial matrices for therapeutic vascularization", Proc. Natl. Acad. Sci. USA, 2010, 107(8): 3323-3328.

Zisch et al., "Cell-demanded release of VEGF from synthetic, biointeractive cell ingrowth matrices for vascularized tissue growth", FASEB J., 2003, 17(5): 2260-2262.

Gao et al., "Ultrafine hydrogel nanoparticles: synthetic approach and therapeutic application in living cells", Angew. Chem. Int. Ed., 2007, 46(13): 2224-2227.

Gao et al., "Bioeliminable nanohydrogels for drug delivery", Nano Lett., 2008, 8(10): 3320-3324.

Yan et al., "A novel intracellular protein delivery platform based on single-protein nanocapsules", Nat. Nanotechnol., 2010, 5(1): 48-53.

West et al., "Polymeric biomaterials with degradation sites for proteases involved in cell migration", Macromolecules 1999, 32(1): 241-244.

Lei et al., "The spreading, migration and proliferation of mouse mesenchymal stem cells cultured inside hyaluronic acid hydrogels", Biomaterials, 2011, 32(1): 39-47.

Lutolf et al., "Repair of bone defects using synthetic mimetics of collagenous extracellular matrices", Nat. Biotechnol., 2003, 21(5): 513-518.

Shireman et al., "Modulation of vascular cell growth kinetics by local cytokine delivery from fibrin glue suspensions", J. Vasc. Surg., 1999, 29(5): 852-862.

Tokatlian et al., "Protease degradable tethers for controlled and cell-mediated release of nanoparticles in 2-and 3-dimensions", Biomaterials, 2010, 31(31): 8072-8080.

\* cited by examiner (A)

(B)

SEQUENCE LISTING

<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Asn Arg Val Lys
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Ile Pro Val Ser Leu Arg Ser Gly Gly Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Val Pro Leu Ser Leu Tyr Ser Gly Gly Lys
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Leu Gly Pro Ala Lys
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Val Pro Arg Gly Ser
1               5

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 6

Gly Cys Arg Glu Gly Pro Gln Gly Ile Trp Gly Gln Glu Arg Cys Gly
1               5                   10                  15
```

ENZYME RESPONSIVE NANOCAPSULES FOR PROTEIN DELIVERY

REFERENCE TO RELATED APPLICATIONS

This application claims the benefit under 35 U.S.C. Section 119(e) of U.S. Provisional Patent Application Ser. No. 61/530,661, filed on Sep. 2, 2011, entitled "ENZYME RESPONSIVE POLYMERIC NANOCAPSULES FOR PROTEIN DELIVERY", the contents of which are incorporated herein by reference.

SEQUENCE LISTING

The instant application contains a Sequence Listing which has been submitted electronically in ASCII format and is hereby incorporated by reference in its entirety. Said ASCII copy, created on Mar. 23, 2016, is named G&C30435.241-US-WO_SL.txt and is 1,733 bytes in size.

STATEMENT OF GOVERNMENT SUPPORT

This invention was made with Government support under Grant No. EB009516, awarded by the National Institutes of Health. The Government has certain rights in the invention.

FIELD OF THE INVENTION

This disclosure generally relates to degradable nanocapsules containing polypeptides. Methods of making and using such nanocapsules are disclosed.

BACKGROUND OF THE INVENTION

Delivering proteins to replace malfunctioning ones or to direct or regulate normal biological functions holds great promises for a broad spectrum of applications ranging from therapeutics, tissue engineering to other areas (see, e.g. D. E. Golan, et al. *Nat. Rev. Drug Discovery* 2008, 7, 21). However, while various delivery approaches have been established, developing the capability to deliver proteins according to local environmental changes, e.g., pH (see, e.g. D. J. Irvine, et al. *Nano Lett.* 2007, 7, 3056; D. J. Irvine, et al. *Biomacromolecules* 2009, 10, 756), and glucose (see, e.g. K. Kataoka, et al. *J. Am. Chem. Soc.* 1998, 120, 12694) and enzyme concentrations (see, e.g. K. S. Anseth, et al. *Biomaterials* 2009, 30, 6048; O. Franssen, et al. *J. Controlled Release* 1999, 59, 219) remains highly challenging.

It is known that biological systems often secrete specific enzymes in response to certain cellular events such as injury or disease (see, e.g. J. S. Powell, et al. *Science* 1989, 245, 186; L. L. Ji, *Med. Sci. Sport Exercise* 1993, 25, 225). If such enzymes could be used to trigger a polypeptide delivery system to release its protein cargoes, proteins could be delivered based on specific cellular events or environmental changes. Moreover, because enzymes are generally highly specific and secreted with precise spatial and temporal control; such an enzyme-responsive delivery can allow protein delivery with spatial and temporal control, factors which provide huge opportunities for tissue engineering and other applications.

The ability to control the delivery of agents into selected physiological environments is desirable. For example, growth factors (GF) such as vascular endothelial growth factor are widely used in tissue engineering applications to induce and guide blood vessel formation. However, the incorporation of GFs into matrices such as hydrogel scaffolds typically results in a loss of GF activity due to reactions between the GF and the reactive hydrogel precursors. For example, the introduction of GF to Michael addition crosslinked hydrogels that use dithiol-containing peptides for crosslinking results in a reduction of disulfide bridges in the encapsulated GF and reduced protein activity (see, e.g. Lutolf, M. P. et al. *Nat Biotechnol* 2003, 21, 513-518; Lutolf, M. P. & Hubbell, J. A. *Biomacromolecules* 2003, 4, 713-722; Lutolf, M. P., et al. *Bioconjug Chem* 2001, 12, 1051-1056; Zisch, A. H. et al. *Faseb J* 2003, 17, 2260-2262; Elbert, D. L. & Hubbell, J. A. *Biomacromolecules* 2001, 2, 430-441; Elbert, D. L., et al. *J Control Release* 2001, 76, 11-25).

Conventional technologies for protein delivery from matrices such as hydrogel scaffolds rely mainly on attaching protein-containing polymer microspheres to hydrogel scaffolds or directly immobilizing protein covalently or electrostatically to hydrogel scaffolds (see, e.g. A. M. Gopferich, et a. *Adv. Drug Delivery Rev.* 2007, 59, 274; K. Ladewig, *Expert Opin. Drug Delivery* 2011). The use of enzymatic action for protein delivery is limited to bulk hydrogels containing enzyme-responsive linkers, which can be cleaved off by specific enzymes to release their protein cargos (see, e.g. K. Ladewig, *Expert Opin. Drug Delivery* 2011; J. L. West, et al. *Biomaterials* 2010, 31, 3840; A. J. Garcia, et al. *Proc. Natl. Acad. Sci. USA* 2010, 107, 3323; A. H. Zisch, et al. *FASEB J.* 2003, 17, 2260). Nano-hydrogels have been synthesized using micro-emulsion polymerization for the general purpose of drug delivery (see, e.g. R. Kopelman, et al. *Angew. Chem. Int. Ed.* 2007, 46, 2224; R. Kopelman, et al. *Nano Lett.* 2008, 8, 3320). However, the synthesis of such nano-hydrogels has been generally achieved in reaction media containing a significant amount of organic solvent and surfactant, forbidding effective incorporation of active proteins within such nano-hydrogels.

There is a general need for methods and materials that can protect polypeptides such as proteins from certain environments, while simultaneously allowing them to function in other environments. The invention disclosed herein addresses these and other needs while overcoming many of the drawbacks and disadvantages of conventional methodologies.

SUMMARY OF THE INVENTION

Embodiments of the invention include methods of making and using compositions comprising a polymer shell that encapsulates one or more polypeptides. In embodiments of the invention, the structure of the shell is designed in a manner that allows it to release the polypeptide(s) into selected environments. In typical embodiments of the invention, polymer components of the shell are interconnected by crosslinked moieties that comprise amino acid sequences that can be cleaved by one or more proteases. In such embodiments of the invention, nanocapsule linkages are designed to maintain the integrity of the polymer shell under one set of environmental conditions, yet simultaneously posses an ability to degrade under another set of environmental conditions, for example, conditions where the environment includes a protease that cleaves amino acid sequences present in the crosslinked moieties of the nanocapsules. This proteolytic degradation compromises the integrity of the polypeptide shell and results in the polypeptide cargo being released from the nanocapsule. Illustrative embodiments of the invention include methods for using compositions of the invention for delivery of polypeptides, such as human vascular endothelial growth factor (VEGF)

into selected environments (e.g. an in vivo environment in which the modulation of vascularization is desired). By utilizing, for example, the variety of different proteases that are present in different environments, a variety of polypeptide delivery systems can be made.

The invention disclosed herein has a number of embodiments. Illustrative embodiments of the invention include methods of controlling the release of a polypeptide from a polymeric nanocapsule into a selected environment. In these methods, artisans can use polymeric nanocapsules formed from a mixture comprising the polypeptide, polymerizable monomers, an initiator that reacts with the polymerizable monomers so as to generate polymers, a first crosslinking agent that links the polymers, wherein the first crosslinking agent is selected to comprise a peptide having an amino acid sequence that is cleaved by a protease, and a second crosslinking agent that links the polymers, wherein the second crosslinking agent does not comprise a peptide having an amino acid sequence that is cleaved by the protease. In these methods, the nanocapsule is designed so that protease mediated cleavage of the peptide in the first crosslinking agent degrades the polymeric nanocapsule so as to release the polypeptide cargo from the polymeric nanocapsule and allow it to migrate in to the external environment. In this embodiment of the invention, the polymeric nanocapsules are placed into an environment selected to include a protease that cleaves the amino acid sequence of the peptide. The protease in the selected environment is then allowed to cleave the amino acid sequence of the peptide, thereby releasing the polypeptide from the polymeric nanocapsule into the selected environment. Typically in these methods, the relative molar amounts of the first crosslinking agent and the second crosslinking agent used in the mixture are selected to control the rate at which the polypeptide is released from the polymeric nanocapsule into the selected environment. In certain embodiments of the invention, polymeric nanocapsules used in these methods are disposed within a matrix comprising a hydrogel. Optionally, the polymeric nanocapsules are covalently coupled to the hydrogel (e.g. via crosslinking agent disclosed herein).

Another embodiment of the invention is a method of forming a polymeric nanocapsule around a polypeptide, wherein the polymeric nanocapsule is designed to release the polypeptide into an environment that includes one or more proteases. These methods comprise forming a reaction mixture that includes the polypeptide of interest (e.g. a growth factor such as vascular endothelial growth factor), a plurality of polymerizable monomers, a first crosslinking agent comprising a peptide having an amino acid sequence that is cleaved by a protease and a second crosslinking agent does not comprise a peptide having an amino acid sequence that is cleaved by the protease. These methods further comprise allowing the plurality of polymerizable monomers and the crosslinking agents to adsorb to surfaces of the polypeptide and then initiating polymerization of the plurality of polymerizable monomers and the first and second crosslinking agents at interfaces between the monomers and the polypeptide. In this way, proteolytically degradable polymeric nanocapsules are formed around one or more polypeptides. In certain embodiments of the invention, polymeric nanocapsules used in these methods are formed to be part of a matrix comprising a hydrogel. Optionally, the polymeric nanocapsules are covalently coupled to the hydrogel (e.g. via crosslinking agent disclosed herein).

Yet another embodiment of the invention is a composition of matter comprising a constellation of chemical groups that are arranged in the composition to form proteolytically degradable polymeric nanocapsules. Typically these compositions include at least one polypeptide and a polymeric network, wherein polymers in the polymeric network are coupled together by a first crosslinking agent and a second crosslinking agent so as to form a shell that encapsulates the polypeptide. In such compositions, the first crosslinking agent comprises a peptide having an amino acid sequence that is cleaved by a protease, and the second crosslinking agent does not comprises a peptide having an amino acid sequence that is cleaved by the protease. In such compositions, the polymers, the first crosslinking agent and the second crosslinking agent are disposed within the polymeric network in an orientation so that proteolytic cleavage of the first crosslinking agent releases the polypeptide from the shell into an external environment. As discussed in detail below, in certain embodiments of the invention, this composition of matter comprises a hydrogel.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 1 illustrates representative schematics of synthesis of the nanocapsules and their controlled release process: (I) enriching the monomers and crosslinkers around the protein surface, (II) forming a polymer shell around the protein molecules by in-situ polymerization leading to the formation of protein nanocapsules, and (III) degrading of the polymer shell by protease releasing their protein cargo. FIG. 1 discloses "KNRVK" as SEQ ID NO: 1.

FIG. 2 illustrates a characterization of nVEGF. (A) Size of the VEGF nanocapsules (nVEGF) synthesized at VEGF: monomer (V:M) molar ratio of 1:6000. (B) Transmission electron microscopic (TEM) image of nVEGF synthesized at V:M molar ratio of 1:6000. (C) Stability of a 35-nm-size nVEGF monitored by Dynamic Light Scattering (DLS) in pH 7.4 PBS buffer at 4° C. Over 8 days, no aggregation is observed.

FIG. 3 illustrates the VEGF nanocapsules (nVEGF) control and release. (A) SDS-PAGE of the degradation of BSA nanocapsules prepared with different ratios of degradable and non-degradable crosslinkers with and without 30 min. plasmin treatment (left to right): ladder; (1) native BSA; (2) nBSA before plasmin treatment; (3) 100% nBSA; (4) 50% nBSA; (5) 33% nBSA and (6) 0% nBSA. (B) Degradation rates of nVEGF prepared with different percentages of degradable crosslinker after 30 min. plasmin treatment. (C) Concentrations of VEGF released from the nVEGF prepared with different percentages of degradable crosslinkers with (shadow) and without (blank) the presence of plasmin. (D) SDS-Page of the specific degradation of 100% nBSA (left to right): ladder; (1) BSA; (2) $nBSA_{NRV}$, (3) $nBSA_{NRV}$+0.2 mg/mL plasmin, (4) $nBSA_{NRV}$+50 unit/mL collagenase; (5) $nBSA_{LGPA}$+0.2 mg/mL plasmin. FIG. 3(B) discloses "KNRVK" as SEQ ID NO: 1.

FIG. 4 illustrates the activity of released VEGF from nanocapsules. (A) Activity of released VEGF tested by adding to human umbilical vein endothelial cells (HUVECs) and running western blotting. (B) Analysis of the western blotting based on the band intensities showing phosphorylated percentage of pVEGF-2. FIGS. 4(A) and (B) disclose "KNRVK" as SEQ ID NO: 1.

FIG. 5 illustrates the protection of nanocapsules in hydrogels by providing a schematic and data showing nVEGF encapsulation onto hydrogels. (A) Scheme of hydrogel formation by Michael addition reaction between bis-cysteine containing crosslinkers and vinyl-group-containing polymers in the presence of nVEGF. (B) Percentages of disulfide bond remained and normalized adsorption intensities/properties of VEGF and nVEGF after exposure to DTNB with or without HS-PEG-SH (exposure to HS-PEG-SH and DTNB versus those exposed to DTNB alone at different VEGF:HS-PEG-SH and nVEGF:HS-PEG-SH molar ratios). The graph illustrates the protection of nVEGF from the thiol attack from dithiol polymer. $Y_2$-axis:percentage of intramolecular disulfide bonds in VEGF remained; $Y_1$-axis:normalized absorption intensity in Ellman's assay of VEGF or nVEGF after exposure to varying HS-PEG-SH. (C) Fluorescence intensities of PBS buffer after placing HA hydrogels that incorporated 3.5 pmol FITC-labeled BSA or its nanocapsules (nBSA) in 400 μL buffer solution at different times. Graphed data shows leaching into PBS buffer of unretained nBSA-FITC in HA hydrogel.

Figure 8:
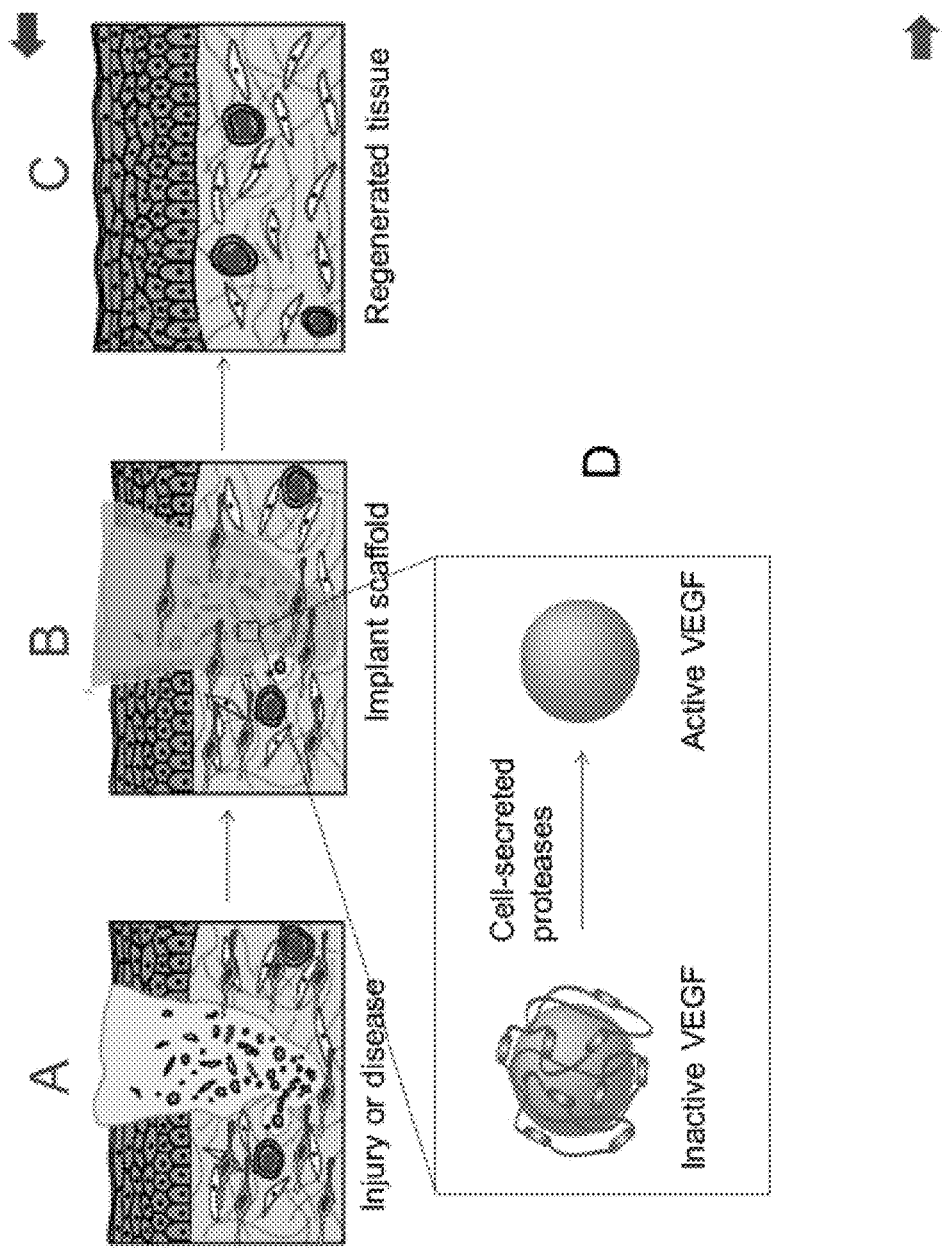

FIG. 8 illustrates an exemplary approach to achieve sustained VEGF release. VEGF will be encapsulated in a nano hydrogel (nVEGF). nVEGF is inactive and is made active by cell released proteases. VEGF is protected from environment (crosslinking) nVEGF can be retained within a hydrogel or not.

Figure 9:
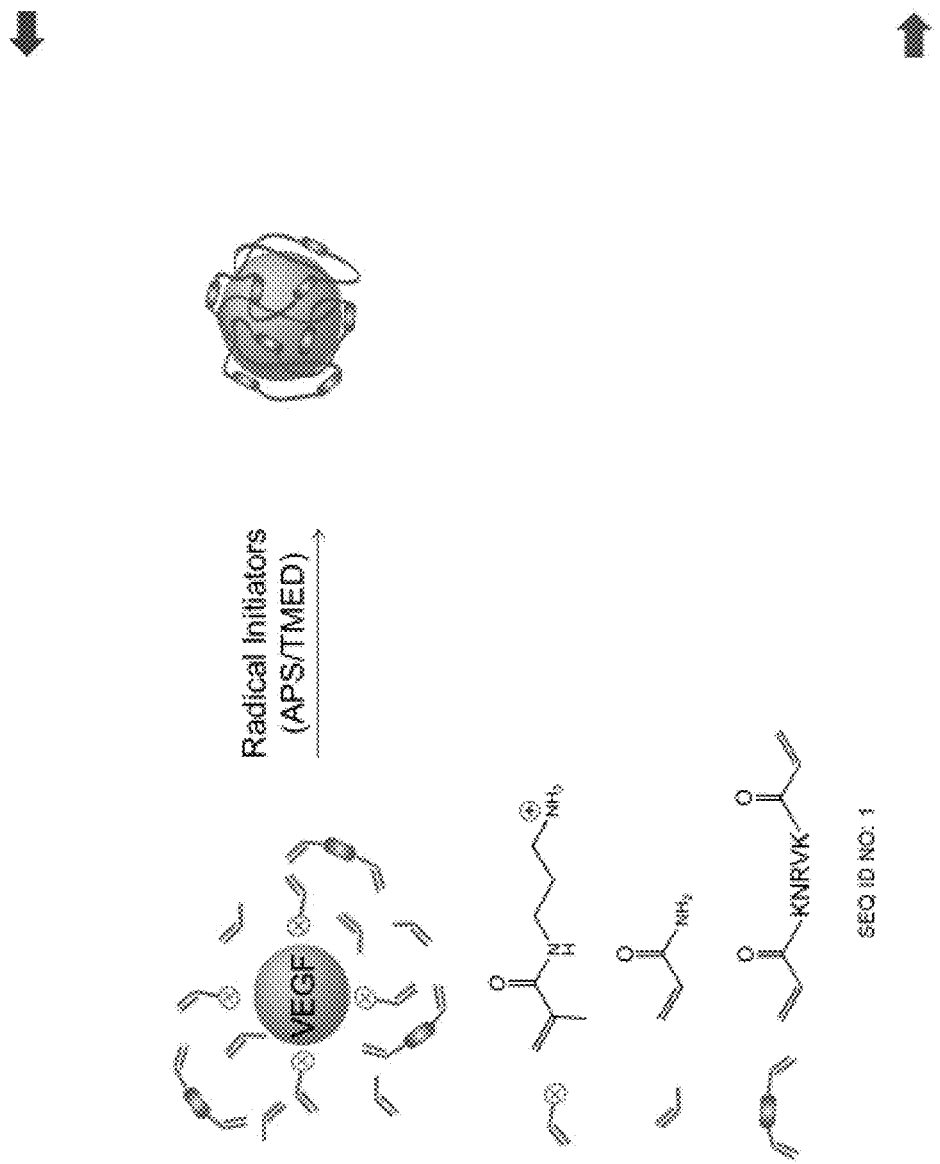

FIG. 9 illustrates an embodiment of the synthesis of growth factor nanocapsules. FIG. 9A shows synthesis schematics, while FIG. 9B shows chemical structures of monomers and crosslinkers. FIG. 9(B) discloses "KNRVK" as SEQ ID NO: 1.

Figure 10:
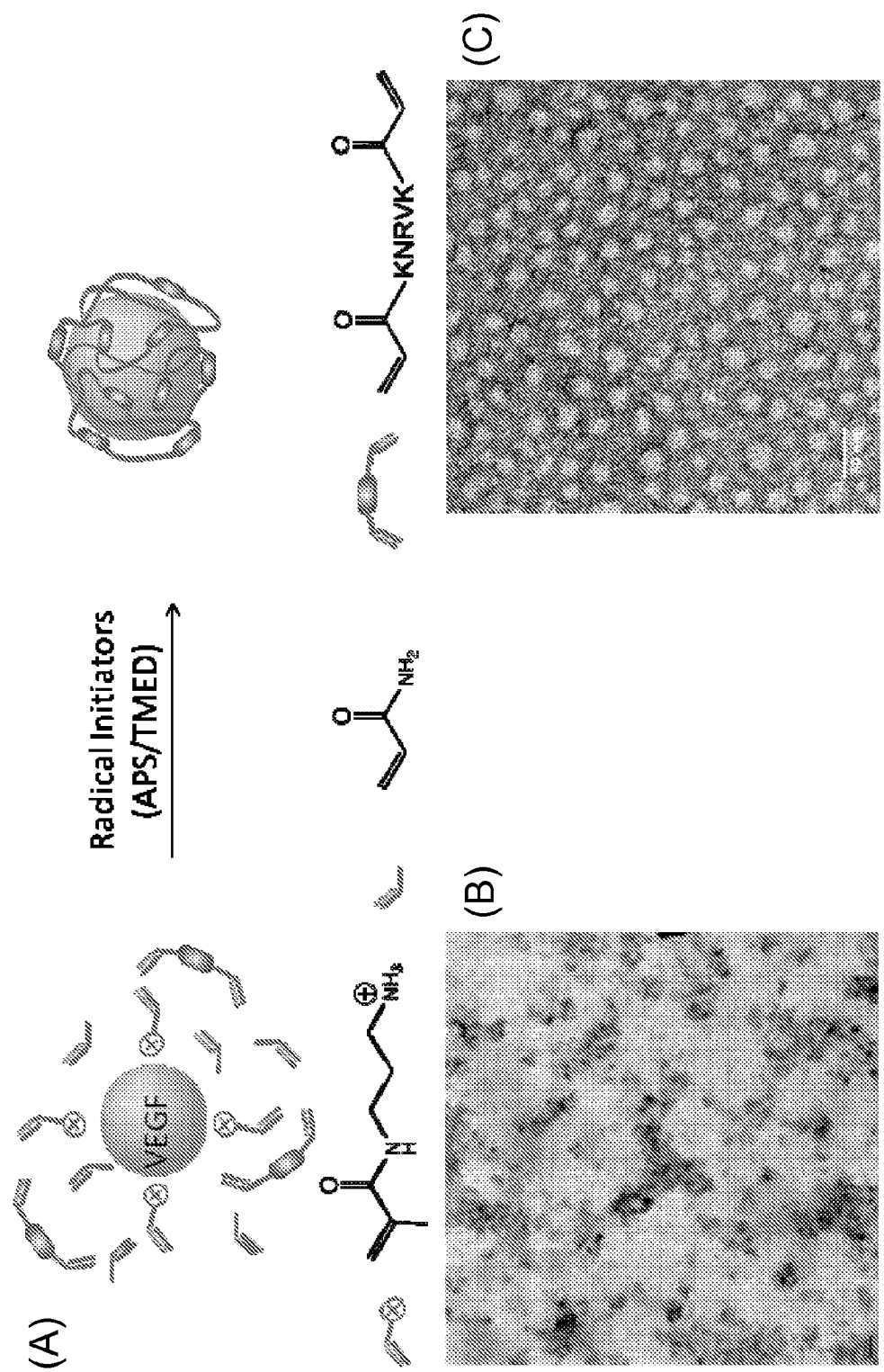

FIG. 10 illustrates an embodiment of the sustained release VEGF nanocapsules. FIG. 10A shows a synthesis scheme with chemical structures. FIG. 10B shows a TEM image of naked VEGF before encapsulation. FIG. 10C shows a TEM image of encapsulated VEGF (nVEGF). FIG. 10(C) discloses "KNRVK" as SEQ ID NO: 1.

Figure 11:
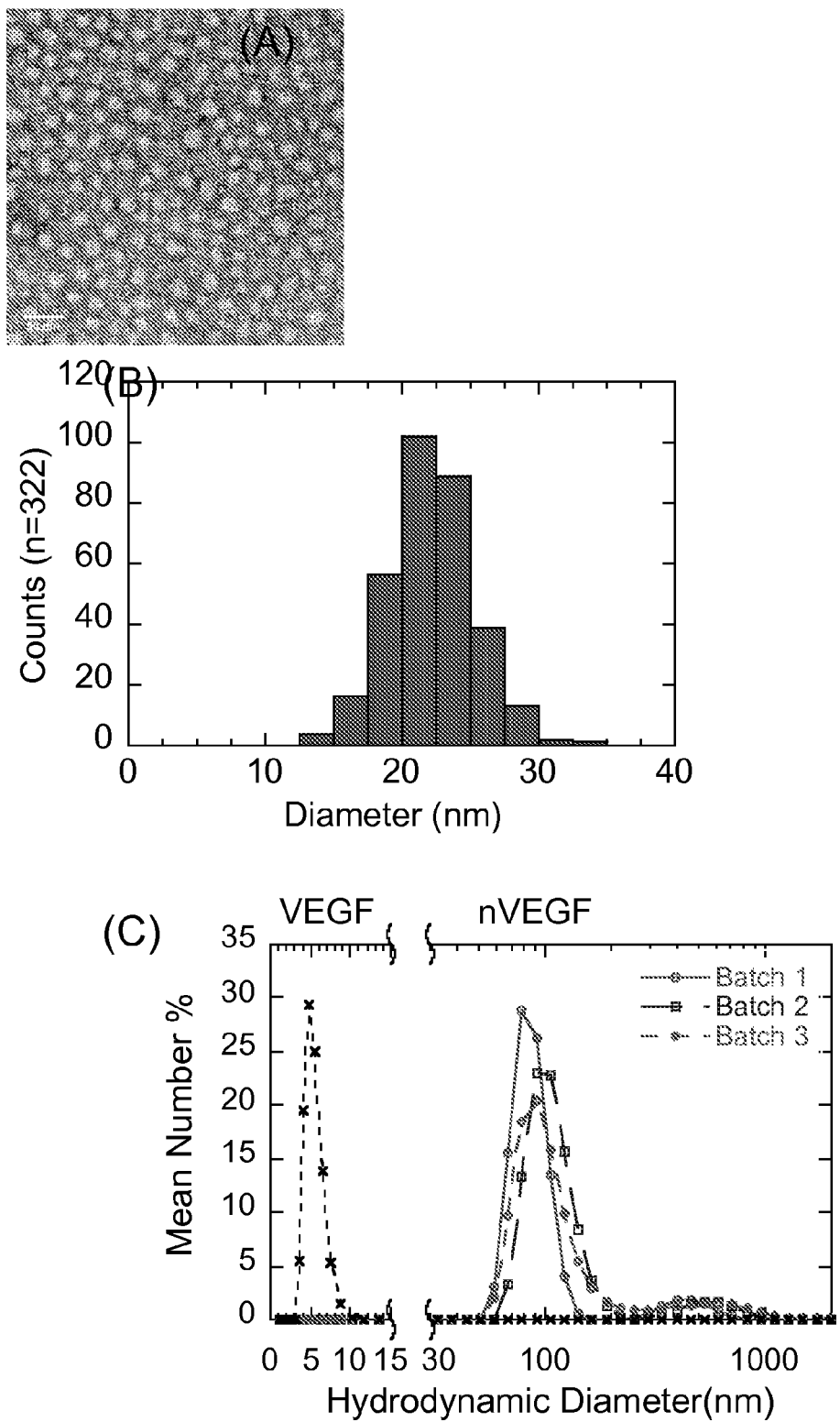

FIG. 11 provides data showing nVEGF characterization, including the size and morphology of nVEGF. (A) Transmission electron microscopic (TEM) image of nVEGF. (B) Size distribution of nVEGF measured from TEM images. (C) Hydrodynamic sizes from dynamic light scattering (DLS).

Figure 12:
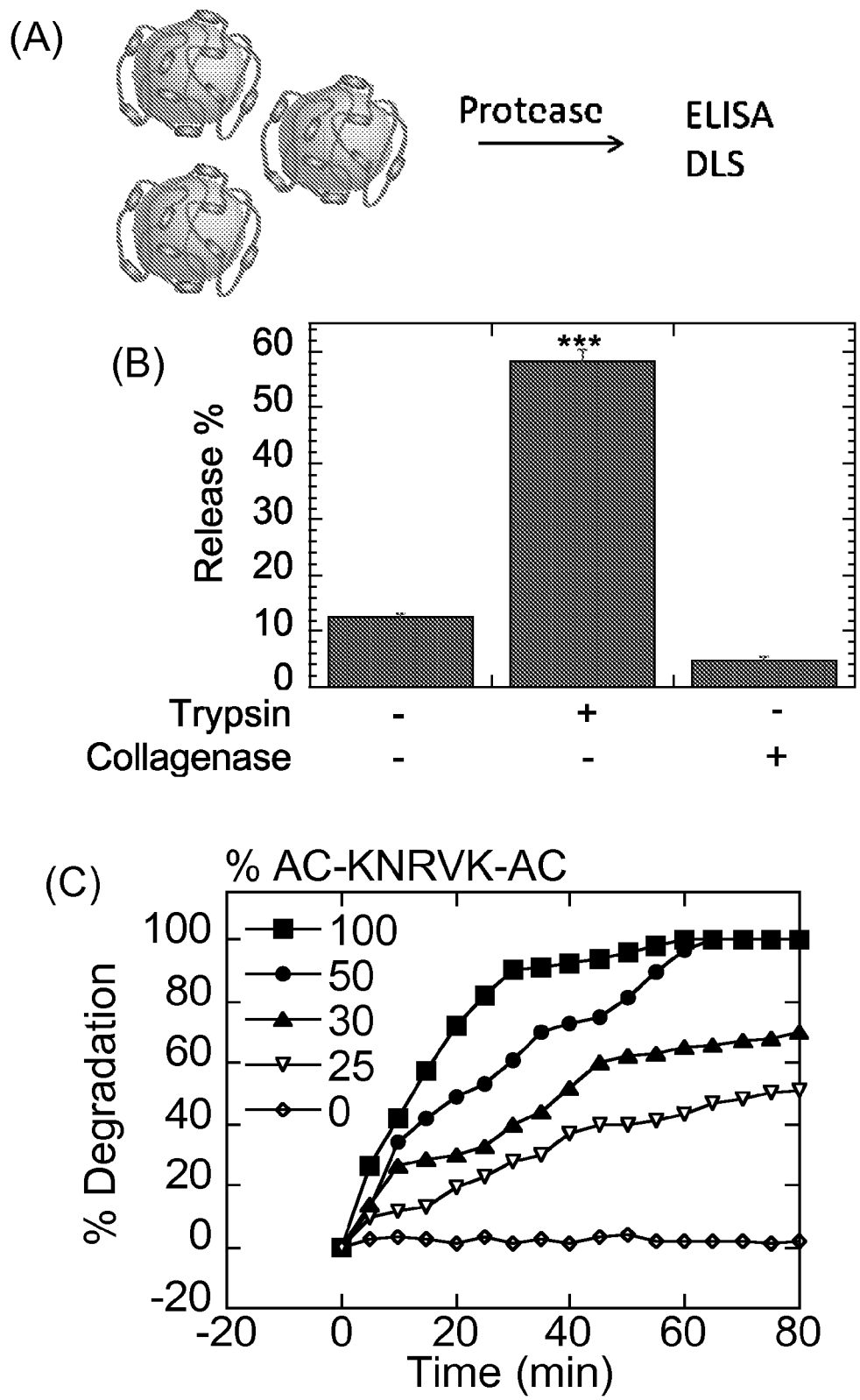

FIG. 12 provides data showing controlled nVEGF degradation through proteases. (A) Schematic of controlled nVEGF degradation through proteases. (B) VEGF release from nVEGF (100% plasmin-sensitive crosslinker) with specific proteases. (C) Degradation rates of nVEGF prepared with different percentages of degradable crosslinker after 30 min plasmin treatment (in the presence of plasmin tested from DLS). FIG. 12(C) discloses "KNRVK" as SEQ ID NO: 1.

Figure 13:
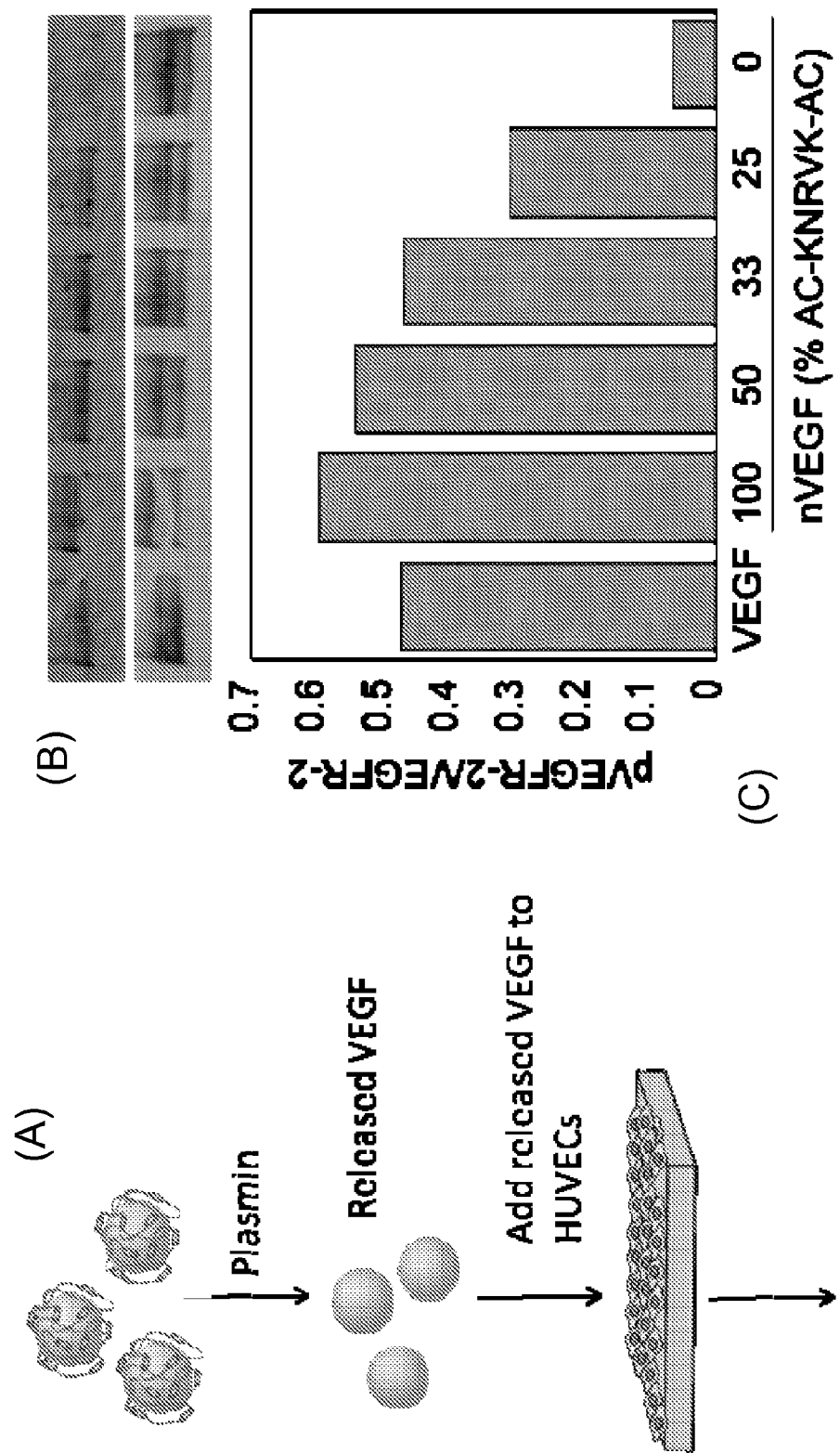

FIG. 13 provides data showing the biological activity of VEGF released from nVEGF. (A) Schematic showing biological assay for measuring VEGF release from nVEGF. (B) Activity of released VEGF tested by adding to HUVECs and western blotting. Activity of released VEGF from de-nVEGF in activating VEGFR-2 to become phosphorylated. (C) Analysis of the western blotting based on the band intensities showing phosphorylated percentage of pVEGF-2. Quantification of phosphorylation intensities seen in B. FIG. 13(C) discloses "KNRVK" as SEQ ID NO: 1.

Figure 14:
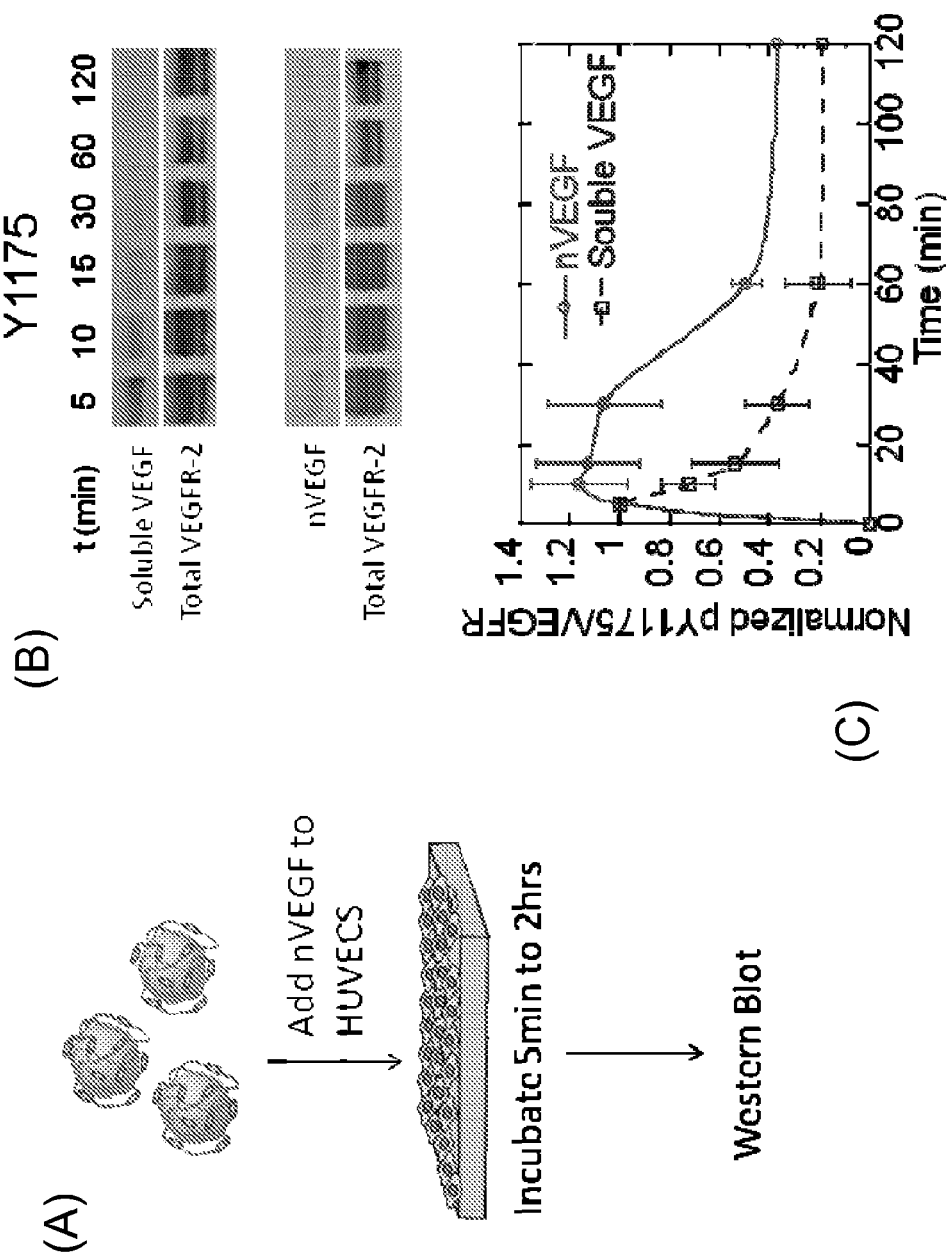

FIG. 14 provides a schematic and data showing that cell-released proteases can degrade nVEGF. A) Schematic showing biological assay for measuring VEGF release from nVEGF following nanocapsule degradation by cell-released proteases. This disclosure shows that cell-produced proteases continuously degrade nanocapsules and released VEGF prolongs the phosphorylation of pVEGFR-2. (B) Western blotting (WB) of phosphorylation of tyrosine residue (1175) on VEGFR on HUVECs after incubation with nVEGF or VEGF (both at 50 ng/mL). (C) Analysis of band intensities and quantification of bands from western blotting (WB) (n=3).

Figure 15:
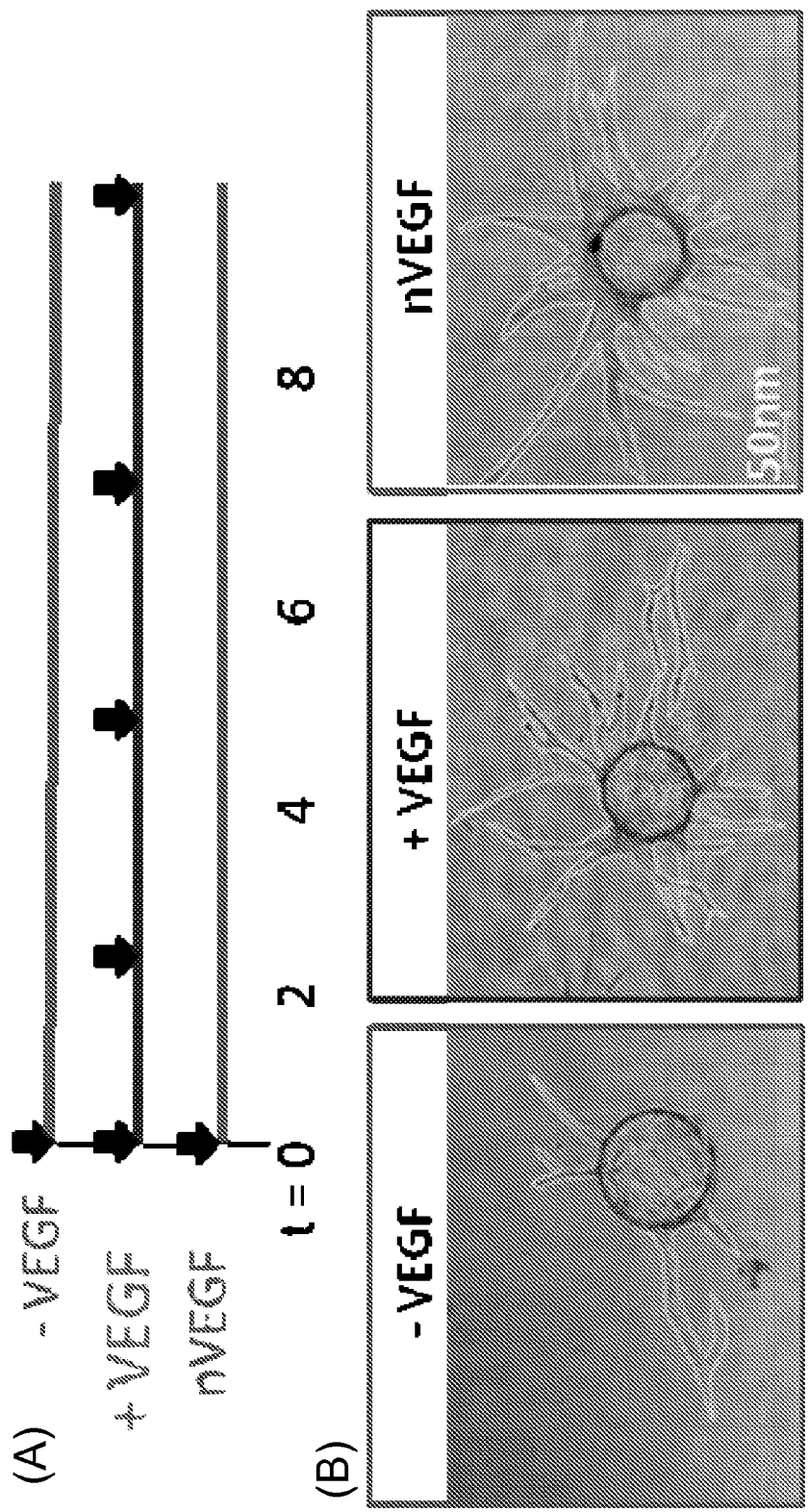

FIG. 15 provides a schematic and data showing how nVEGF sustains activation of HUVECs over 8 days, specifically that nVEGF embedded in fibrin gel sustains the sprouting of HUVECs over 8 days with no replenishing (n=3×5). (A) Schematic of conditions: non-replenishing nVEGF at 200 ng/mL, non-replenishing VEGF at 200 ng/mL and replenishing VEGF at 2.5 ng/mL. (B) HUVEC sprouting within 3D fibrin hydrogel containing de-nVEGF, VEGF and replenishing VEGF. Images of HUVEC sprouts at day 8, fluorescently stained with rhodamine-phalloidin for F-actin and DAPI for nuclei.

Figure 16:
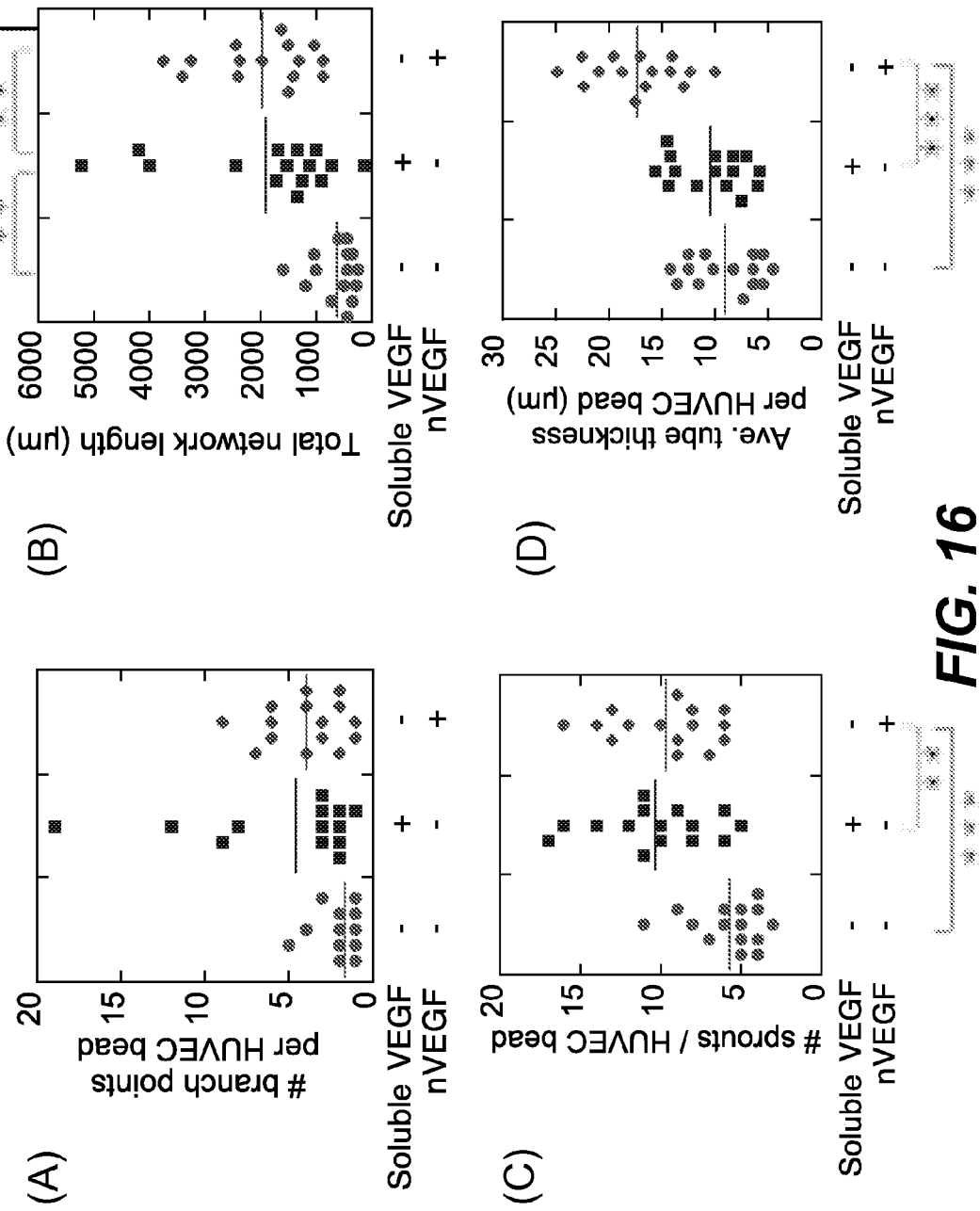

FIG. 16 provides graphical data showing characterizing how nVEGF sustains activation of HUVECs over 8 days. Statistical analysis of sprout measurements. (One-way ANOVA, and Tukey HSD as post hoc test. n=15,  p<0.01, * p<0.001.)

Figure 17:
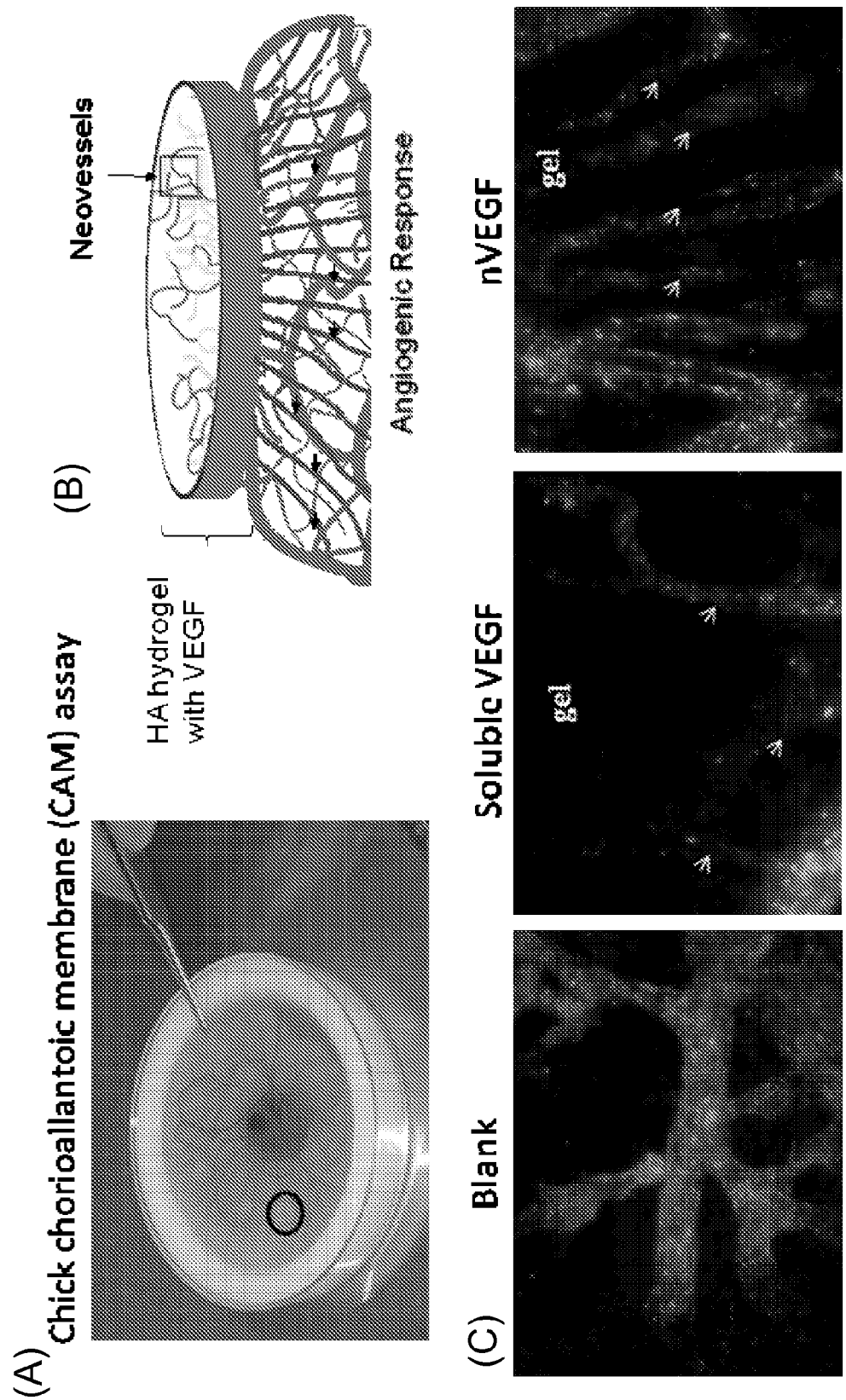
Figure 18:
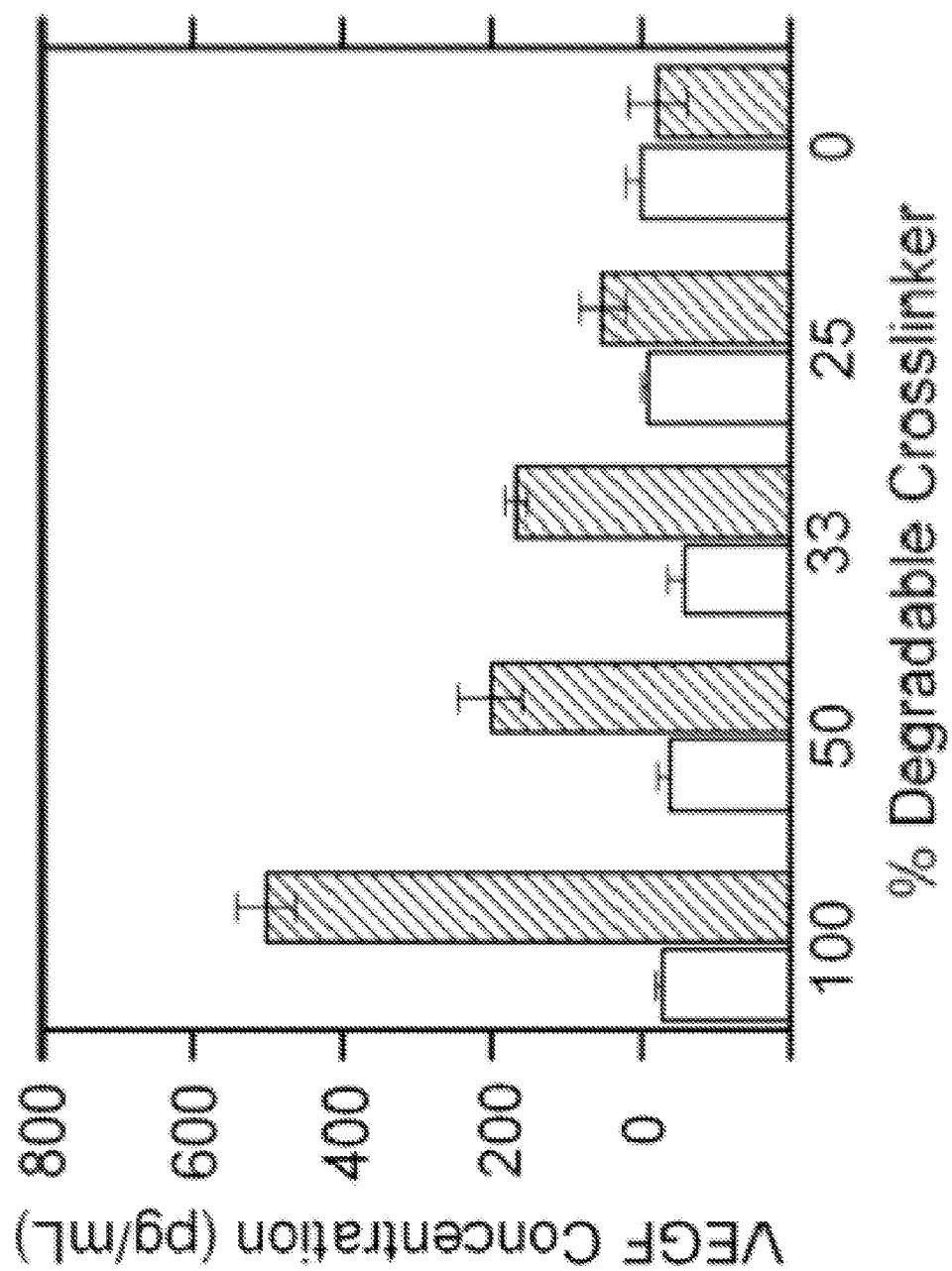

FIG. 17 provides data which illustrates nVEGF activity in an in vivo angiogenesis assay, specifically nVEGF induced capillary formation radially from a hyaluronic acid (HA) gel implant comprising encapsulated nVEGF or soluble VEGF FIG. 18 illustrates released VEGF from degradation of nVEGF prepared with varying percentage of degradable crosslinkers by plasmin (shadow) versus no plasmin (blank) in ELISA.

Figure 19:
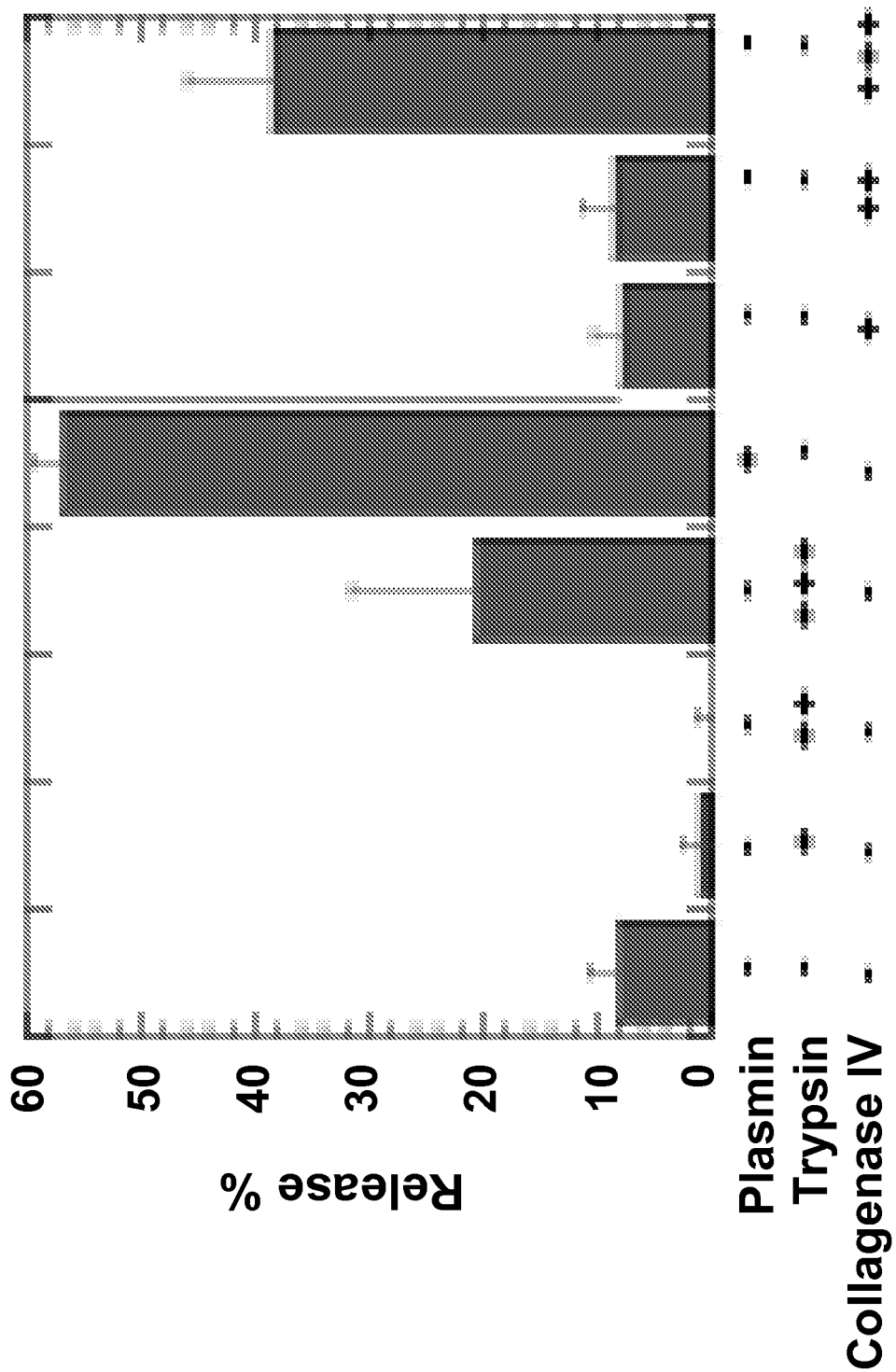

FIG. 19 illustrates enzyme-linked immunosorbent assay showing nVEGF prepared with 100% plasmin-degradable crosslinker (de-nVEGF$_{plasmin100}$) can be degraded to release cargo VEGF with plasmin, trypsin and collagenase IV (containing a low tryptic activity). ("++", "+++": 20, 30 min).

Figure 20:
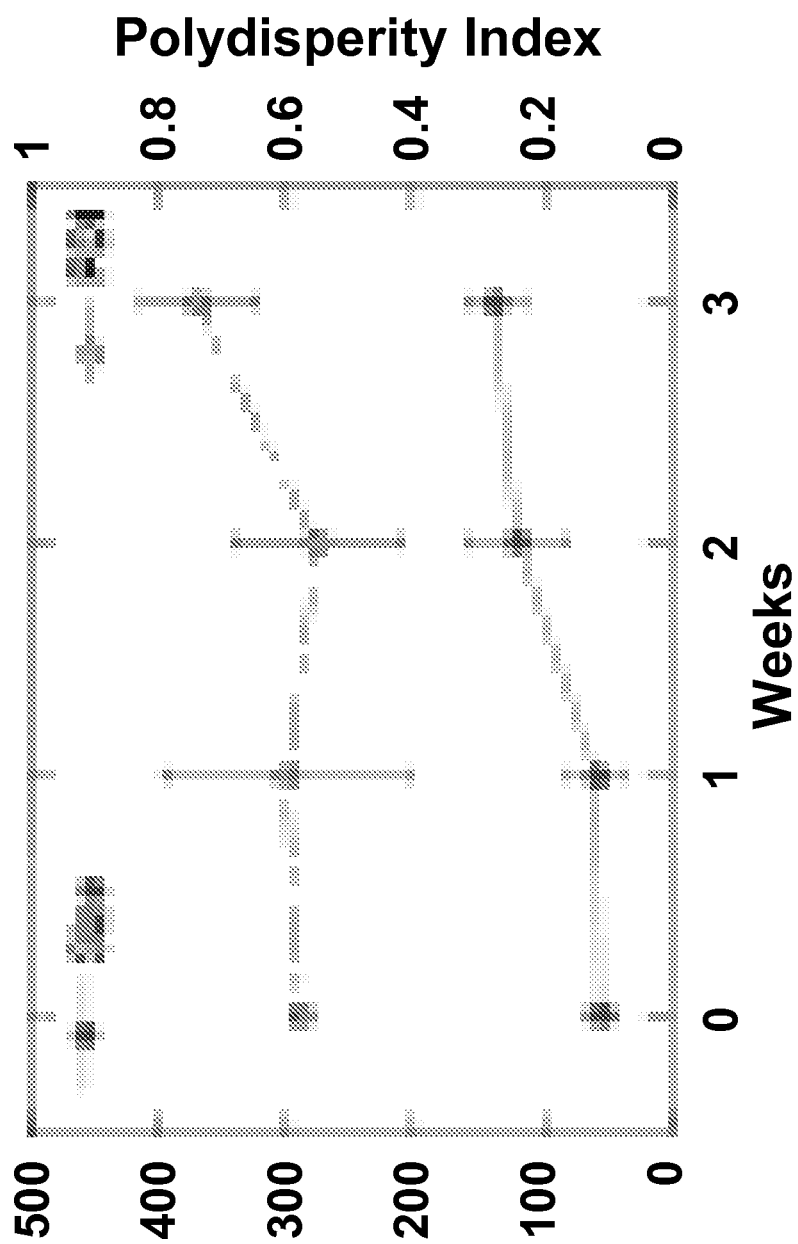

FIG. 20 illustrates the stability of de-nVEGF$_{plasmin}$ stored in pH 7 phosphate buffer at 4° C. monitored by DLS. Continued measurements up to 3 weeks show some aggregation in week 2.

Figure 21:
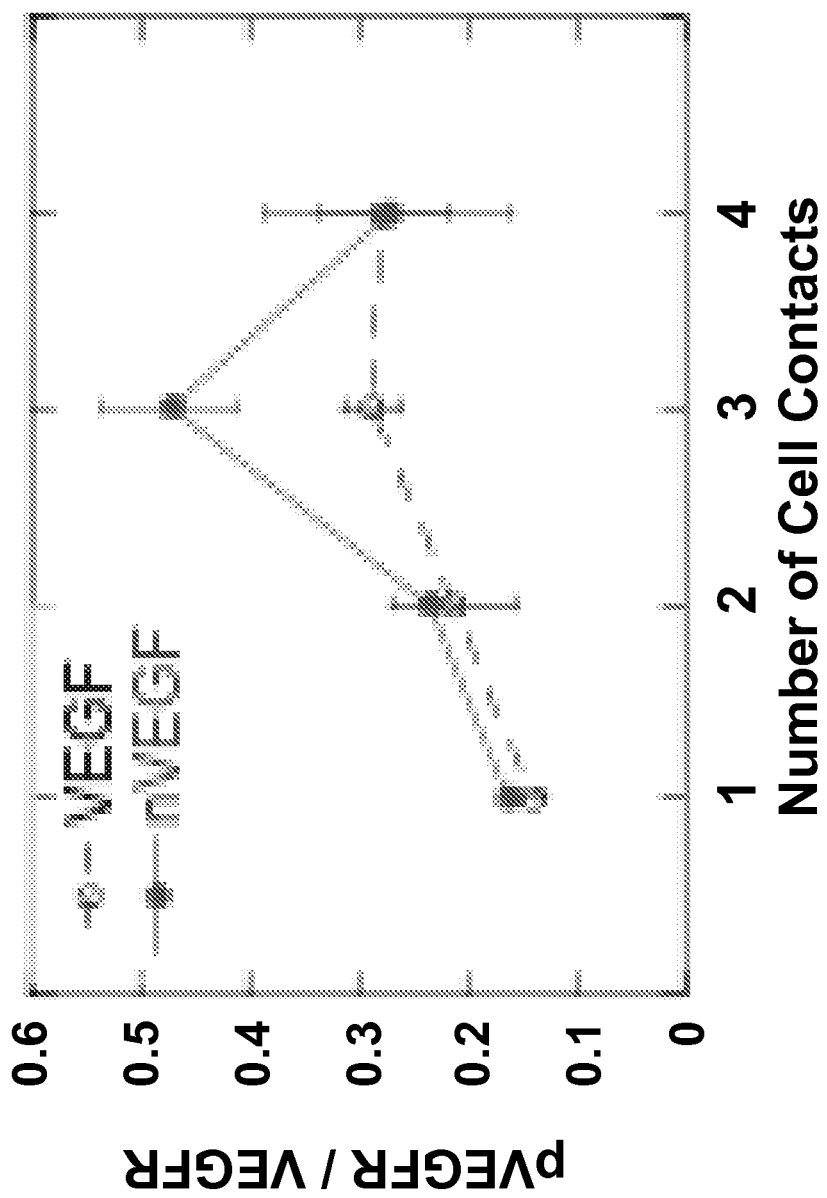

FIG. 21 illustrates the cell-demanded release of nVEGF sustains the activation of VEGF-receptor (VEGFR) on HUVECs. PathScan VEGFR ELISAs of a number of 4 sets of HUVECs treated sequentially with one same nVEGF (50 ng/mL), each for 30 min (n=3).

Figure 22:
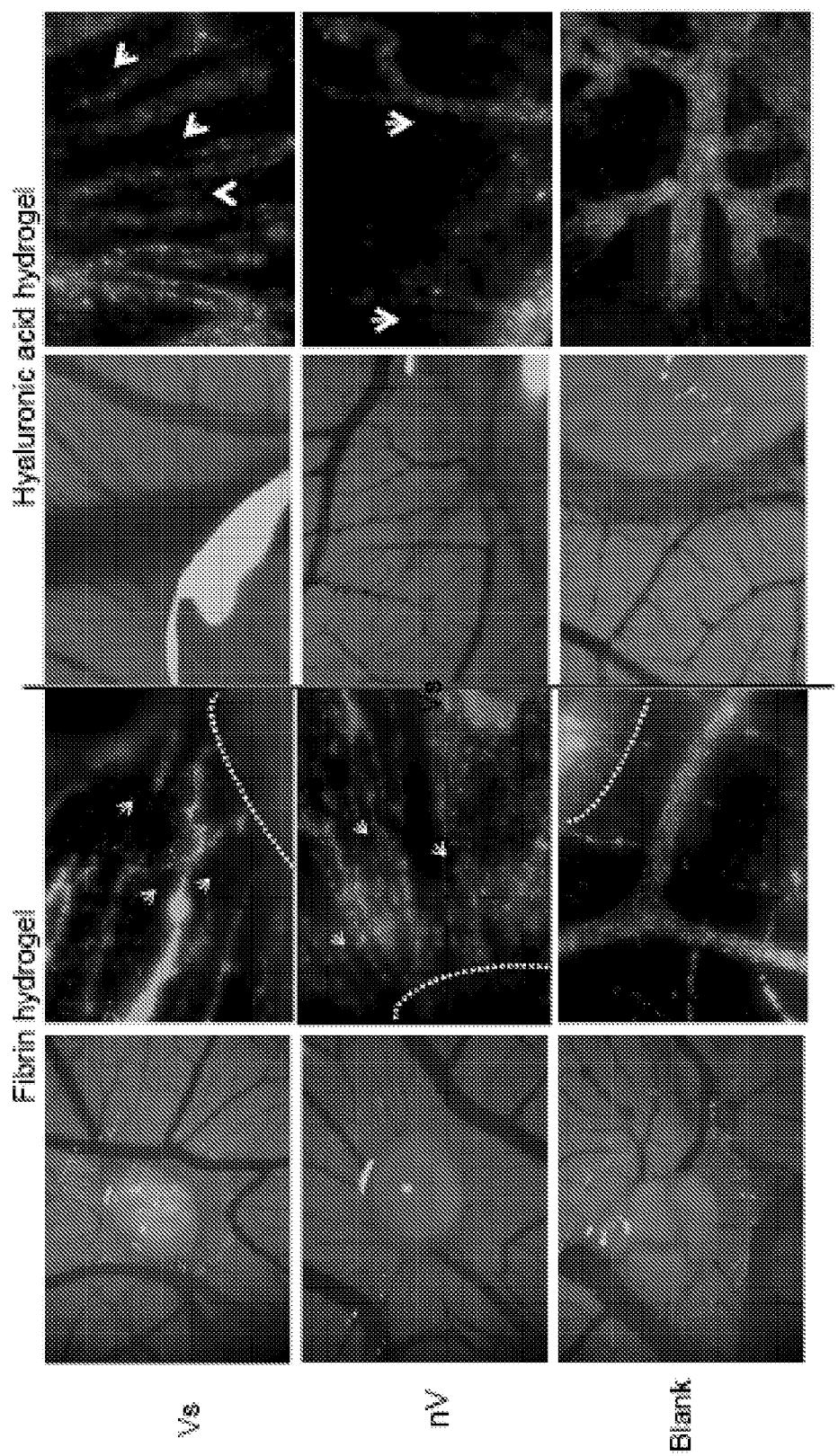

FIG. 22 illustrates hydrogels containing nVEGF that are able to induce neovascularization after being implanted on the chick embryo chorioallantoic membrane for 2 days. Three rows of images, from top to bottom, represent hydrogels containing nVEGF 1 μg/mL, soluble VEGF 1 μg/mL and none. Two types of hydrogels were implanted: (left) fibrin hydrogel of a final concentration 2 mg/mL of fibrin, (right) hyaluronic acid hydrogel of 3% (w/v). Fluorescent images were taken after fixation and perfusion of CAMs with FITC-dextran via intravenous injection.

Figure 23:
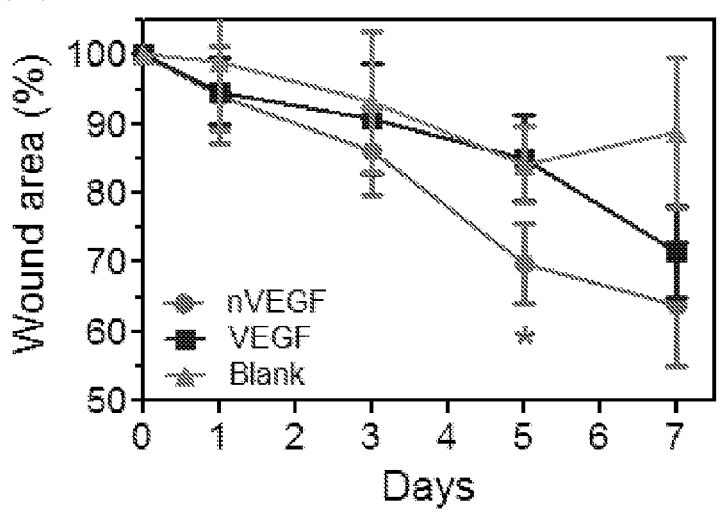
Figure 23:
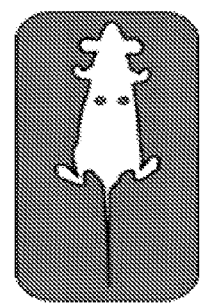
Figure 23:
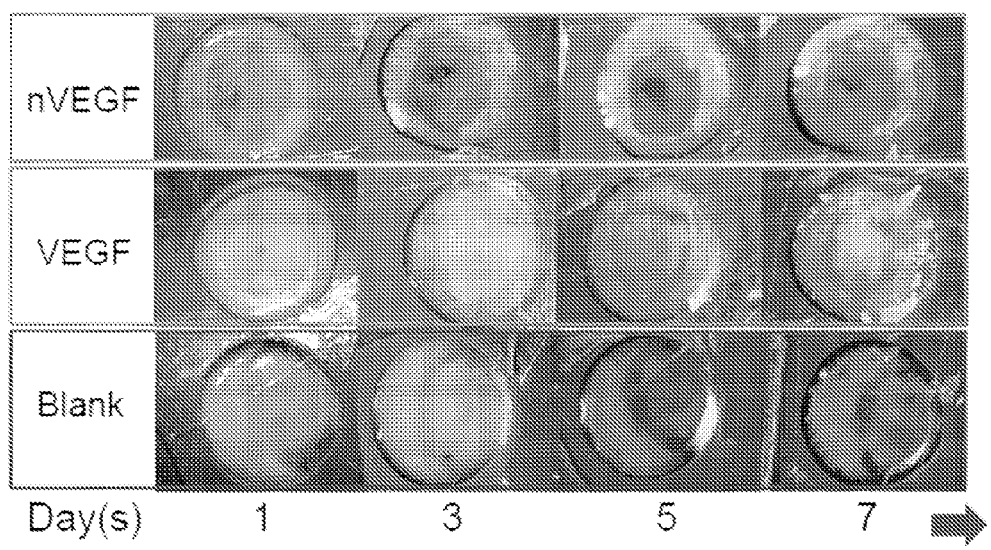

FIG. 23 shows in vivo data on wound healing in mice administered VEGF in redox response nanocapsules. Specifically, FIG. 23 shows mouse wound closure rate with implants of fibrin gel with nVEGF, VEGF or no VEGF. (A) Wound closure profile measured. (n=4; 3 for Blank). Results are given as mean±SD; Kruskal-Wallis one-way analysis and all pair Dunns post test (n=4; 3 for Blank. * P<0.05). (B) Microscopic images of wounds monitored every other day.

Figure 24:
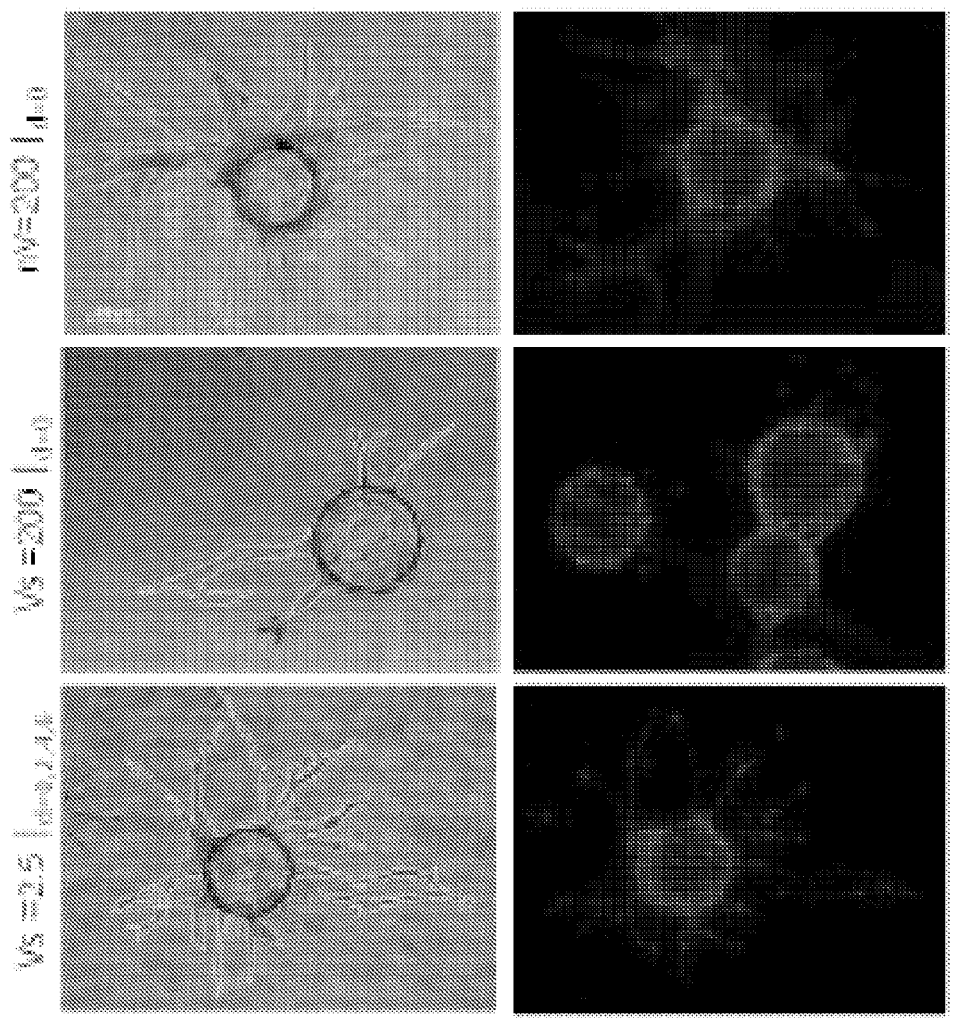

FIG. 24 illustrates HUVEC sprouting within 3D fibrin hydrogel containing de-nVEGF, VEGF and replenishing VEGF. Illustrated are images of HUVEC sprouts at day 8, fluorescently stained with rhodamine-phalloidin for F-actin and DAPI for nuclei.

DETAILED DESCRIPTION OF THE INVENTION

Unless otherwise defined, all terms of art, notations and other scientific terms or terminology used herein are intended to have the meanings commonly understood by those of skill in the art to which this invention pertains. Many of the techniques and procedures described or referenced herein are well understood and commonly employed using conventional methodology by those skilled in the art. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification. In the description of the embodiments, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The invention disclosed herein relates to nanocapsules that can be tuned to release agents such as polypeptides into selected environments. In various embodiments of the invention, compositions of matter and methods are provided, for example, to protect a protein cargo within a nanocapsule from a first environment; to incorporate proteins into tissue engineering scaffolds without loss of protein activity; and to deliver inside or outside a cell. Embodiments of the invention include methods of forming a polymeric nanocapsule disposed around one or more polypeptides, wherein the nanocapsule is designed to degrade in certain environments thereby releasing the polypeptides. Typically these methods include forming a mixture comprising a polypeptide, a plurality of polymerizable monomers; and a crosslinking agent that includes a plurality of amino acids linked by peptide bonds in a sequence or "motif" that is recognized and cleaved by a protease. In certain embodiments of the invention, the nanocapsule is designed for use with proteases that recognize amino acid sequences that are at least 5 amino acids in length such as KNRVK (SEQ ID NO: 1), GGIPVSLRSGGK (SEQ ID NO: 2) or GGVPLSLYSGGK (SEQ ID NO: 3). In certain embodiments of the invention, polymeric nanocapsules used in these methods are disposed within a matrix comprising a hydrogel. Optionally, the polymeric nanocapsules are covalently coupled to the hydrogel (e.g. via a crosslinking agent disclosed herein).

In methods of the invention, the nanocapsule forming mixture is exposed to conditions that first allow the plurality of polymerizable monomers and the crosslinking agent to adsorb to surfaces of the polypeptide. Polymerization of the plurality of polymerizable monomers and the crosslinking agent at interfaces between the monomers and the polypeptide is then initiated so that a modifiable polymeric nanocapsule is formed, one that surrounds and protects the polypeptide. Typically, polymerization is initiated by adding a free radical initiator to the mixture and the resultant polymer chains are then linked together via one or more crosslinking agents. In illustrative embodiments of the invention, the crosslinking agent comprises a sequence of amino acids that are linked by peptide bonds, wherein the sequence comprises an amino acid motif that is recognized and cleaved by one or more proteases. In typical embodiments, the polypeptide is not covalently coupled to the polymeric nanocapsule following the polymerization of the plurality of polymerizable monomers and the crosslinking agent, and is free to migrate away from the nanocapsule upon loss of its integrity (e.g. as a result of cleavage of its peptide bonds). Optionally, the mixture comprises a plurality of polypeptides associated within a protein complex (e.g. a multimeric protein complex). In certain embodiments of the invention, polymeric nanocapsules used in these methods are formed within a matrix comprising a hydrogel (e.g. by controlling polymerization conditions).

Embodiments of the invention can incorporate any one of a wide variety of polypeptides known in the art into enzyme responsive nanocapsules, for example, a protein selected for an ability to stimulate vasculogenesis and angiogenesis and/or alter a metabolic pathway of the cell and/or modulate the transcription of one or more targeted genes in the cell. Consequently, in various embodiments of the invention, protease-responsive nanocapsule compositions can be used to shuttle different protein cargos useful for biomedical applications, including regenerative medicine, treating loss-of-function genetic diseases, cancer therapy, vaccination, and imaging (e.g. imaging useful in diagnostic methodologies). As shown in the working examples below, proteins that can stimulate vasculogenesis and angiogenesis such as VEGF can be adapted for use with the methods and materials described herein and be delivered to patients as therapeutic agents. In the working examples below, a polypeptide encapsulated by a polymer shell of the invention is vascular endothelial growth factor (VEGF), a signal protein produced by cells that stimulates vasculogenesis and angiogenesis. Optionally, the nanocapsules are disposed within a hydrogel matrix in a three dimensional architecture selected to modulate one or more physiological processes such as angiogenesis, for example, by releasing growth factors such as VEGF (or anti-growth factor antibodies such as an anti-VEGF antibody (e.g. AVASTIN)). In certain embodiments of the invention, polymeric nanocapsules used in these methods are formed within a matrix comprising a hydrogel (e.g. by controlling polymerization conditions).

Illustrative embodiments of the invention include methods of controlling the release of a polypeptide cargo from a polymeric nanocapsule into a selected environment (e.g. control the rate at which polypeptide is released and/or control/select the specific environment in which polypeptide is released). In these methods, enzyme-responsive protein nanocapsules are synthesized that can release protein cargoes in response to specific enzymes (e.g. proteases secreted during certain cellular events) with a high degree of specificity as well as a controlled rate of release (e.g. by controlling reaction condition so as to tune the material profiles of the nanocapsule compositions). Typically these polymeric nanocapsules are formed from a mixture comprising the polypeptide, polymerizable monomers, an initiator that reacts with the polymerizable monomers so as to generate polymers, wherein the polymers form the polymeric nanocapsule, a first crosslinking agent that links the polymers, wherein the first crosslinking agent is selected to comprise a peptide having an amino acid sequence that is cleaved by a protease, and a second crosslinking agent that links the polymers, wherein the second crosslinking agent does not comprise a peptide having an amino acid sequence that is cleaved by the protease. In certain embodiments of the invention, polymeric nanocapsules are disposed within a three dimensional matrix comprising a hydrogel.

In typical methods of the invention, the nanocapsule is designed so that protease mediated cleavage of the peptide in the first crosslinking agent degrades the polymeric nanocapsule so as to release the polypeptide from the polymeric nanocapsule and allow it to migrate in to the external environment. In these methods, the relative amounts of the first crosslinking agent and the second crosslinking agent in the mixture can be selected to control release of the polypeptide from the polymeric nanocapsule. Further methodological steps in this embodiment of the invention comprise placing the polymeric nanocapsules in an environment selected to include a protease that cleaves the amino acid sequence of the peptide, and then allowing the protease in the selected environment to cleave the amino acid sequence of the peptide, thereby releasing the polypeptide from the polymeric nanocapsule into the selected environment. In certain embodiments of the invention, the protease is produced by a human cell within the selected environment (e.g. an in vivo environment).

Another embodiment of the invention is a method of forming a polymeric nanocapsule around a polypeptide, wherein the polymeric nanocapsule is designed to release the polypeptide into a selected environment. These methods comprise forming a mixture that includes the polypeptide of interest (e.g. a growth factor such as vascular endothelial growth factor), a plurality of polymerizable monomers, a first crosslinking agent comprising a peptide having an amino acid sequence that is cleaved by a protease and a second crosslinking agent does not comprise a peptide having an amino acid sequence that is cleaved by the protease. These methods further comprise allowing the plurality of polymerizable monomers and the crosslinking agents to adsorb to surfaces of the polypeptide and then initiating polymerization of the plurality of polymerizable monomers and the first and second crosslinking agents at interfaces between the monomers and the polypeptide. In this way, proteolytically degradable polymeric nanocapsules are formed around one or more polypeptides. In certain embodiments of the invention, the polymeric nanocapsule is formed from a mixture further comprising a third crosslinking agent that links a first polymer with a second polymer, wherein the third crosslinking agent comprises a peptide having an amino acid sequence that is cleaved by a protease. As discussed herein, embodiments of the invention can be adapted for use with a wide variety of proteases. In illustrative embodiments of the invention, amino acid sequence that is cleaved by the protease comprises a sequence cleaved by plasmin such as KNRVK (SEQ ID NO: 1), or a sequence cleaved by matrix metalloproteinase such as GGIPVSLRSGGK (SEQ ID NO: 2) or GGVPLSLYSGGK (SEQ ID NO: 3).

Yet another embodiment of the invention is a composition of matter comprising a constellation of elements that are arranged in the composition to form proteolytically degradable polymeric nanocapsules. Typically these compositions include at least one polypeptide and a polymeric network, wherein polymers in the polymeric network are coupled together by a first crosslinking agent and a second crosslinking agent so as to form a shell that encapsulates the polypeptide. Optionally in these embodiments, the shell that encapsulates the polypeptide has a diameter between 15 and 35 nanometers. In typical compositions, the first crosslinking agent comprises a peptide having an amino acid sequence that is cleaved by a protease, and the second crosslinking agent does not comprises a peptide having an amino acid sequence that is cleaved by the protease. In such compositions, the polymers, the first crosslinking agent and the second crosslinking agent are disposed within the polymeric network in an orientation so that proteolytic cleavage of the first crosslinking agent releases the polypeptide from the shell into an external environment. A wide variety of polypeptides can form the cargo of the polymeric nanocapsules disclosed herein. Optionally, for example, the polypeptide is a protein that stimulates cellular growth such as VEGF. In certain embodiments, the protein is an antibody. In some embodiments of the invention, the protein induces cellular death (e.g. via an apoptosis pathway).

In some embodiments of the invention, the polypeptide within the nanocapsule is selected for an ability to alter a metabolic pathway of cells. Illustrative non-limiting examples of metabolic pathways include purine metabolism pathway, pyrimidine metabolism pathway, alanine, aspartate and glutamate metabolism pathway, glycine, serine and threonine metabolism pathway, cysteine and methionine metabolism pathway, valine, leucine and isoleucine degradation pathway, valine, leucine and isoleucine biosynthesis pathway, lysine biosynthesis pathway, lysine degradation pathway, arginine and proline metabolism pathway, histidine metabolism pathway, tyrosine metabolism pathway, phenylalanine metabolism pathway, tryptophan metabolism pathway, phenylalanine, tyrosine and tryptophan biosynthesis pathway, beta-alanine metabolism pathway, taurine and hypotaurine metabolism pathway, phosphonate and phosphinate metabolism pathway, selenocompound metabolism pathway, cyanoamino acid metabolism pathway, D-glutamine and d-glutamate metabolism pathway, D-arginine and d-ornithine metabolism pathway, D-alanine metabolism pathway, and glutathione metabolism pathway. In certain embodiments of the invention, the polypeptide stimulates cellular growth. In other embodiments of the invention, the polypeptide induces cellular death (e.g. via apoptosis).

In certain embodiments of the invention, the nanocapsule encapsulates a cytokine. The term "cytokine" is a generic term for a class of polypeptides released by cells that act as mediators of a wide variety of physiological processes. Examples of such cytokines are lymphokines, monokines, and traditional polypeptide hormones. Included among the cytokines are growth hormones such as vascular endothelial growth factor, epidermal growth factor, human growth hormone, N-methionyl human growth hormone, bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL).

In embodiments of the invention, polymerization of the modified enzymes and monomer unit(s) may use any method suitable for the polymerizable groups used on the protein and monomer unit(s) and which does not destroy the function of the protein during polymerization. Examples of polymerization methods include photopolymerization and free-radical polymerization of double bond containing polymerizable groups. In some embodiments, the polymerization is a free radical polymerization.

In certain methods and compositions of the invention, the relative molar amounts of two or more reagents such as the first and second crosslinkers combined in the polymerization mixture are controlled so as to produce nanocapsules having certain desirable polypeptide release profiles (e.g. so as to release the polypeptide a controlled rate and/or to release the polypeptide over a selected time period). In some embodiments of the invention, relative molar amounts of the first crosslinking agent the second crosslinking agent in the shell are selected to be from 1:1 to 1:100 (e.g. 1:1, 1:2, 1:3, 1:4, 1:5, 1:6, 1:7, 1:8, 1:9, or 1:10, or 1:20, 1:21 etc, up to 1:100). In other embodiments of the invention, relative molar amounts of the first crosslinking agent the second crosslinking agent in the shell are selected to be from 1:1 to 100:1 (e.g. 10:1, 9:1, 8:1, 7:1, 6:1, 5:1, 4:1, 3:1, 2:1 or 1:1, or 20:1, 19:1 etc, up to 100:1). Typically, the relative molar amounts of the first crosslinking agent the second crosslinking agent combined in the mixture are at least 1:5, 1:4, 1:3, 1:2, 1:1, 2:1, 3:1, 4:1 or 5:1. In certain methods and compositions of the invention, the relative molar amounts of the polymerizable monomers and the initiator combined in the mixture are similarly controlled so as to produce nanocapsules having certain desirable material profiles and are between 2000:1 and 8000:1. Typically a concentration of initiator used to make polymers in the reaction is at least 10 µM; and a concentration of 100, 200, 300, 400, 500, 600, 700, 800, 900 or 1000 µM (e.g. 250 µM) can produce consistent nanocapsules with low polydispersities. Lower concentrations of initiator can be used to induce polymeric nanocapsule formation with a high monomer concentration; post-synthesis addition of the initiator up to tens to hundreds of micromoles can re-polymerize monomers of a low concentration to cure the formation of polymeric shell. In some embodiments of the invention, the reaction conditions are controlled in order to produce a fixed monomer-to-VEGF ratio of at least 1000:1, 2000:1 or 3000:1, for example with a monomer concentration of between 6.5-8.5 mM (e.g. 7.9 mM) in such reactions.

In typical embodiments of the invention, proteins are incorporated within nanocapsules, which keep them protected from their environment and enhance their stability. With the use of a capsule shell that is degradable by enzymes present in the extracellular space, the capsules can further be used to deliver proteins to a variety of different environments, for example to an extracellular environment where the protein can activate cell surface receptors. Furthermore, the capsules can be used as robust components of scaffolds for tissue engineering and tissue regeneration. Embodiments of this invention can be used in therapy, tissue engineering and tissue regeneration applications. In certain embodiments of the invention, the composition further comprises a hydrogel in which the shell is disposed. Optionally in such embodiments, the shell is covalently coupled to the hydrogel by a hydrogel crosslinking agent. In some embodiments of the invention, the hydrogel crosslinking agent comprises a peptide having an amino acid sequence that is cleaved by a protease (e.g. a plasmin, a matrix metalloproteinase etc.).

Compositions of the invention can be formulated as a pharmaceutical composition, which comprises a composition of the invention and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like. A pharmaceutical composition or kit of the invention can contain other pharmaceuticals, in addition to the compositions of the invention. The other agent(s) can be administered at any suitable time during the treatment of the patient, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention. One skilled in the art will appreciate that a suitable or appropriate formulation can be selected, adapted or developed based upon the particular application at hand. Dosages for compositions of the invention can be in unit dosage form. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle. One skilled in the art can easily determine the appropriate dose, schedule, and method of administration for the exact formulation of the composition being used, in order to achieve the desired effective amount or effective concentration of the agent in the individual patient.

The dose of a composition of the invention, administered to an animal, particularly a human, in the context of the present invention should be sufficient to effect at least a detectable amount of a diagnostic or therapeutic response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, etc. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Embodiments of the invention are desirable due to their ability to protect polypeptides such as growth factors in vitro and in vivo, thereby extending their therapeutic efficacy beyond that observed with naked proteins (which often have a half life of less than 1 hour in solution). In one exemplary embodiment of the invention, a method is provided to increase growth factor (GF) activity after encapsulation by protecting the GF prior to encapsulation inside the hydrogel. Nanocapsules consisting of a GF core and a thin protease degradable hydrogel shell around it (nGF) provide a protected GF with enhanced stability toward chemical induced inactivation. In certain embodiments, nGF can be formed with multiple different GFs using the same chemistry to form the nanocapsule. The nGF protects the GF from degradation by dithiol containing crosslinkers, and the introduction of protease degradable peptides to the nanocapsule provides a controlled and environmentally-triggered release of the protein cargo. Such an approach is highly innovative and represents a significant leap in current technology since it provides a universal strategy for introducing GFs into hydrogel scaffolds. Current strategies for the incorporation of GFs into hydrogel scaffolds expose the GFs to the crosslinking chemistry and require the chemical modification of the GFs, resulting in reduced GF activity.

Figure 1:
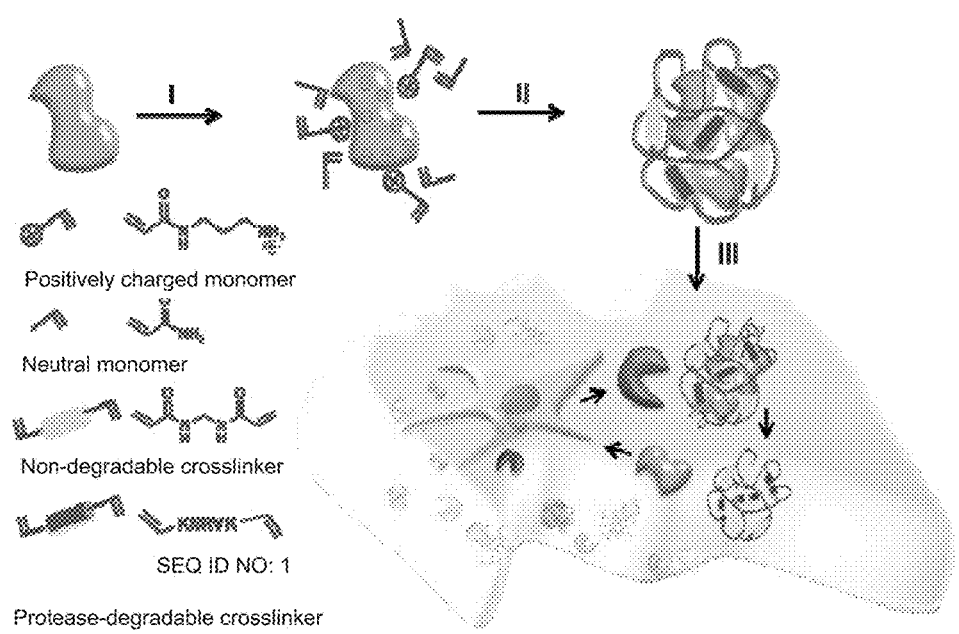

In embodiments of the invention, a novel enzyme-responsive delivery platform with controlled-release capability and specificity based on protein nanocapsules is provided, as illustrated in FIG. 1. In one exemplary embodiment, bovine serum albumin (BSA) and vascular endothelial growth factor (VEGF) is used. VEGF has been proven to be specific and critical for angiogenesis (see, e.g. H. Gerhardt, et al. *J. Cell Biol.* 2003, 161, 1163). It has also been proven that matrix metalloproteinases (MMP) (see, e.g. Y. Okada, et al. *Pathol. Int.* 2010, 60, 477) and serine proteases, such as plasmin (see, e.g. T. Syrovets, et al. *Cell Mol. Life. Sci.* 2004, 61, 873; D. Roth, et al. *Am. J. Pathol.* 2006, 168, 670) are generally up-regulated in diseased or injured tissues. By using such proteases as the trigger, controlled release of VEGF from the nanocapsules can be used to induce and guide blood vessel formation.

The synthesis of the nanocapsules can be achieved using a simple encapsulating technique, as illustrated for example in FIG. 1. In one exemplary embodiment, buffer solutions containing positively charged monomer (N-(3-aminopropyl) methacrylamide (APM)), neutral monomer (acrylamide (AAM)), and non-degradable and protease-degradable cross-linkers are used. Electrostatic and hydrogen-bonding interactions enrich the monomers and crosslinkers around the protein molecules (step I). In situ free-radical polymerization forms a thin polymer layer around the proteins, forming the protein nanocapsules (denoted as nVEGF and nBSA, respectively) with controlled composition (step II) (see, e.g. M. Yan, et al. *Nat. Nanotechnol.* 2010, 5, 48). Tuning the ratio of the positive-charged and the neutral monomers allows the control of nanocapsule surface charge; while tuning the ratios of the degradable peptide and non-degradable crosslinkers allows the synthesis of nanocapsules with tunable degradability. Upon exposure to proteases, the peptide crosslinkers are cleaved off and the nanocapsules release their protein cargo with a controlled release rate (step III).

Figure 2:
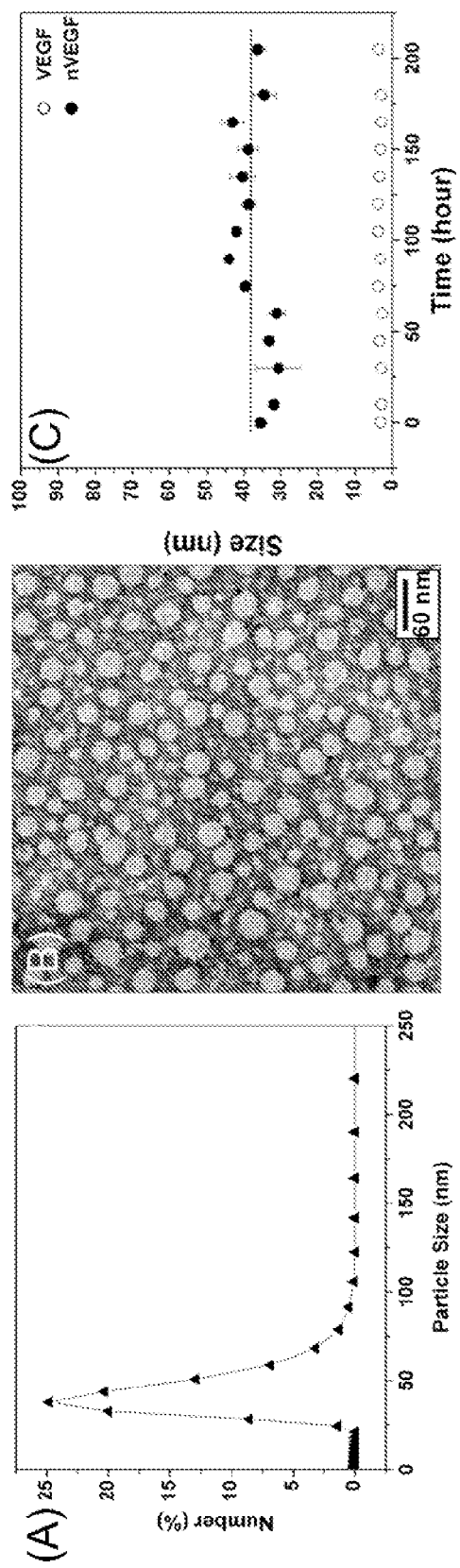

FIG. 2B shows an illustrative transmission electron microscopic (TEM) image of the nanocapsules prepared with a VEGF:monomer ratio of 1:6000 and an APM:AAM: degradable crosslinker molar ratio of 5:5:1. In one exemplary embodiment, these nanocapsules exhibit a zeta potential of +1.4 mV and have diameters ranging from 20 to 45 nm, which is consistent with the dynamic light scattering (DLS) measurement (25~60 nm; FIG. 2A). At this size, the nanocapsules are expected to have multiple proteins per nanocapsule. Note that the surface charge of the nanocapsules can be readily tuned from −7 to +5 mV by adjusting the ratios of the positively charged monomer to other building molecules used (Table 1, provided below). The stability of these nanocapsules can be examined by monitoring their size variation in phosphate buffered saline (PBS) at 4° C. (FIG. 2C). Similar to the native protein, these nanocapsules, with an average diameter of 35 nm, exhibit no obvious aggregation in 8 days, indicating an excellent stability in solution.

TABLE 1

Size and zeta potential of BSA and 100% de-nBSA

| P:M molar ratio | Zeta-potentials (pH = 7.4) | Diameters (nm) |
|---|---|---|
| Native BSA | −16.1 mV | 5.2 |
| 1:3000 | −6.44 mV | 147.3 |
| 1:4500 | −3.71 mV | 72.1 |
| 1:6000 | +1.60 mV | 33.6 |
| 1:7500 | +4.25 mV | 10.9 |

Figure 3:
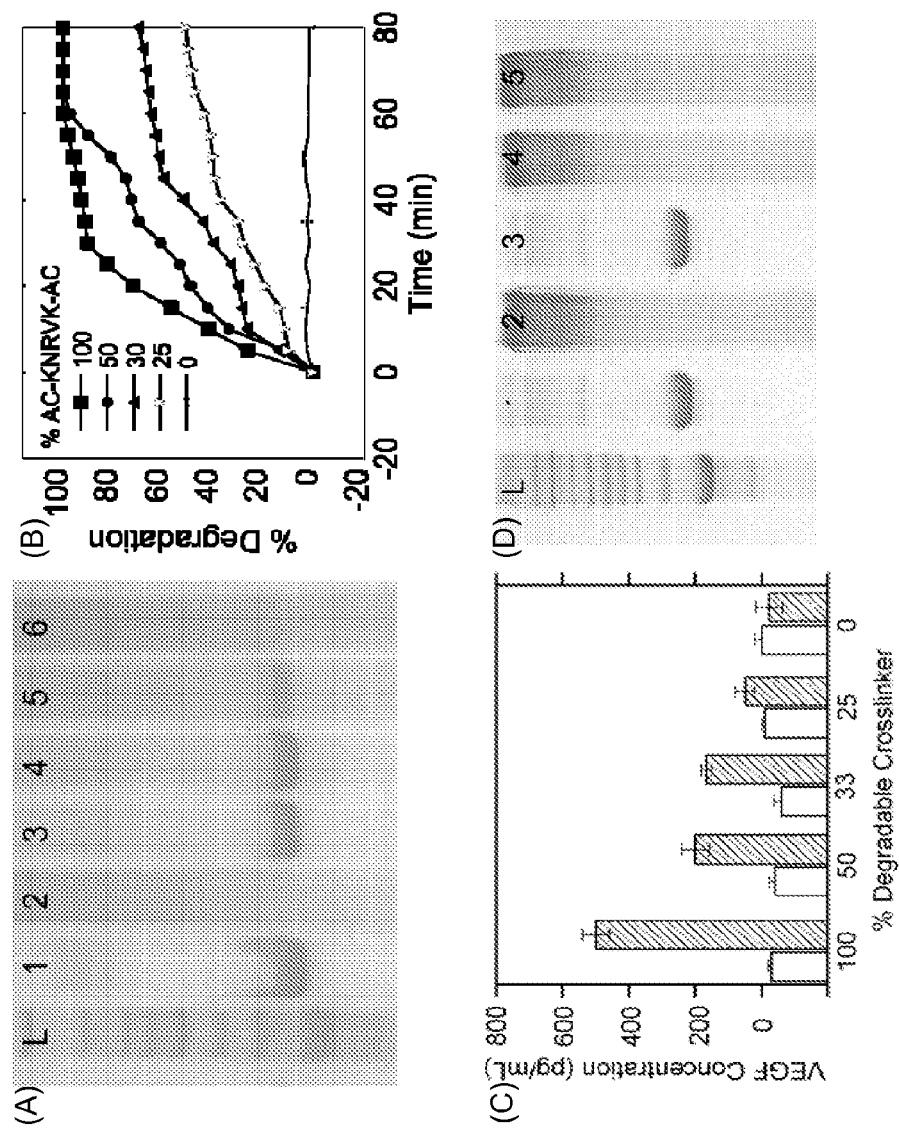

In another embodiment of the invention, the release of the protein from the nanocapsules can be readily controlled by the ratios of degradable crosslinkers to non-degradable crosslinker. In one exemplary embodiment, a plasmin-cleavable crosslinker is synthesized by bisacryloylating a plasmin-specific peptide Lys-Asn-Arg-Val-Lys (KNRVK, SEQ ID NO. 1) (see, e.g. J. A. Hubbell, J. L. West, *Macromolecules* 1999, 32, 241) while N, N'-methylene bisacrylamide (BIS) is chosen as the non-degradable crosslinker. FIG. 3A shows an illustrative sodium dodecyl sulfate polyacrylamide gel electrophoresis (SDS-PAGE) image of (1) native BSA, (2) nBSA prepared with 100% degradable crosslinker without plasmin treatment, and (3-6) nBSA prepared with 100%, 50%, 33%, 25%, and 0% degradable crosslinker, respectively, after treating with 0.2 mg/mL plasmin for 30 min. Compared with the native BSA, which exhibits a well-defined band (line 1), the nBSA is broadly dispersed within the gel, possibly because of their dispersive size and charge distribution (line 2). Exposing the nanocapsules to plasmin degrades the polymer shell, leading to a subsequent release of the BSA that exhibits bands (line 3-5) similar as that of native BSA (line 1). As expected, nBSA prepared using a non-degradable crosslinker (line 6) exhibits a similar pattern as that of the degradable one prior to exposure to plasmin (line 2). This demonstrates the feasibility of encapsulating proteins within the nanocapsules and releasing them responsively by enzymatic degradation of the nanocapsules.

The degradation kinetics of the nanocapsules can be quantified using the DLS technique. Using nVEGF as an example, FIG. 3B shows illustrative degradation profiles of nVEGF prepared with different ratios of degradable cross-linkers in the presence of plasmin. The initial shell thickness of the nVEGF can be estimated from $R_0-R_{VEGF}$, where $R_0$ is the initial diameter of nVEGF and $R_{VEGF}$ is the diameter of a VEGF molecule (~4 nm). The degree of degradation can be described as $[R_0-R_t]/[R_0-R_{VEGF}]*100\%$, where $R_t$ is the time-dependent nVEGF diameter. nVEGF prepared with 100% degradable crosslinkers was degraded completely after 40 min, while for those prepared with 0% degradable crosslinker, no degradation was observed. Note that the slopes of the illustrative degradation profiles consistently increase with the percentage of degradable crosslinkers, confirming increasing degradation rates with an increasing percentage of the degradable crosslinkers.

Figure 6:
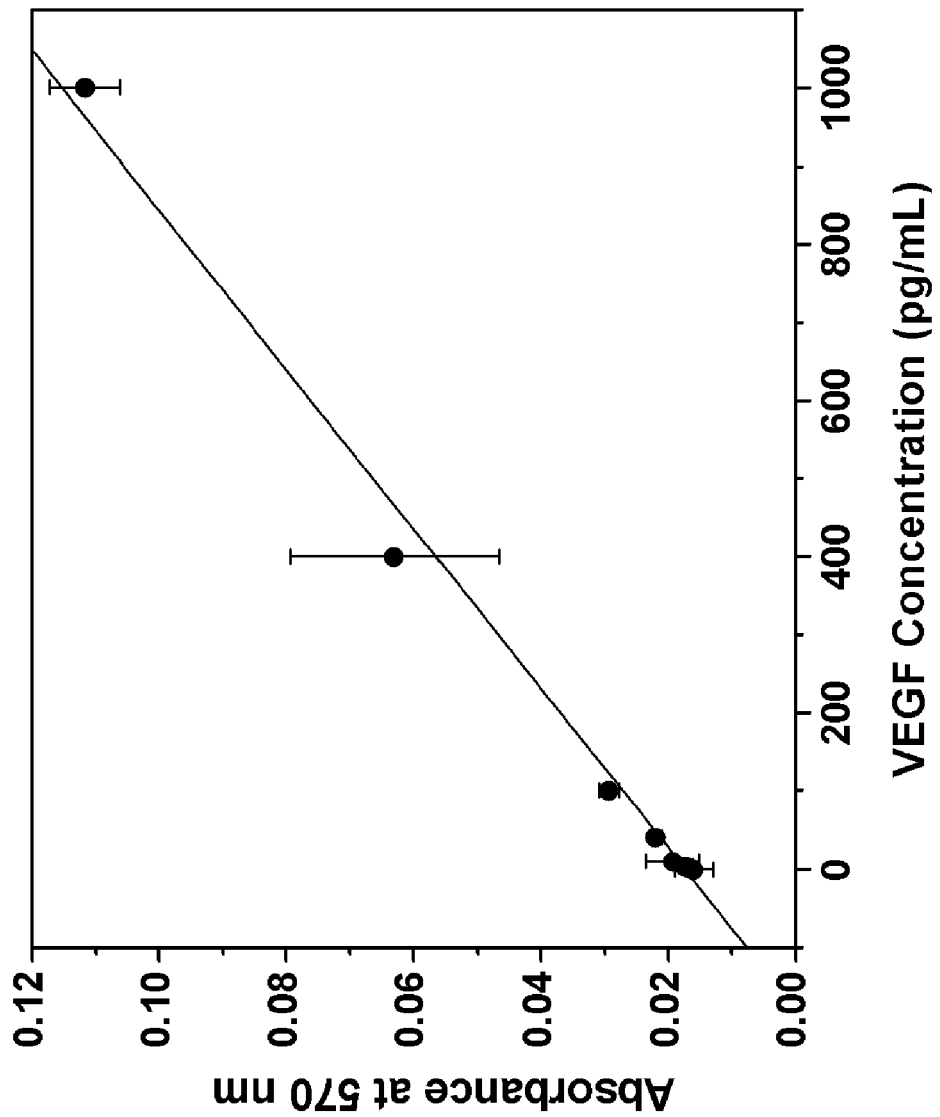
FIG. 6 illustrates an absorbance-concentration standard plot of VEGF based on ELISA test.
Figure 7:
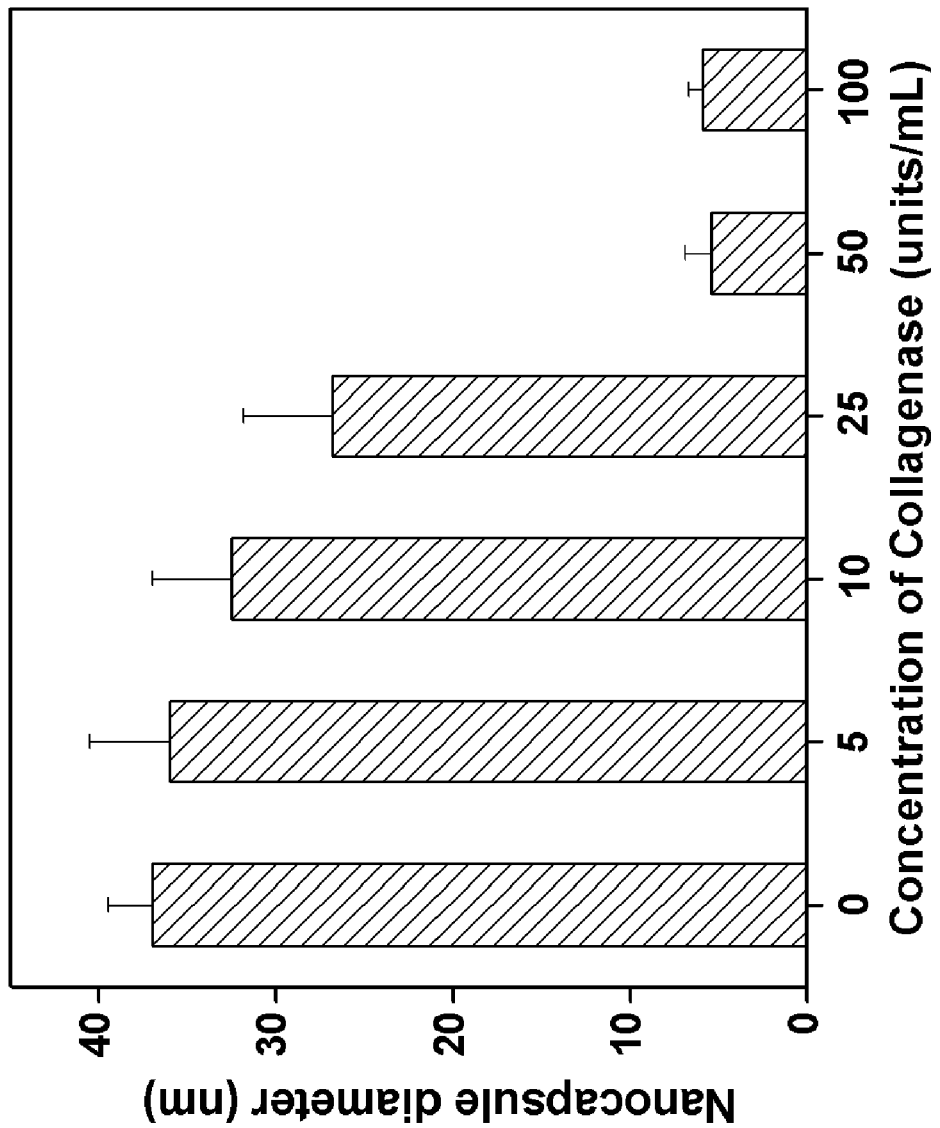
FIG. 7 illustrates various sizes of nBSA with a matrix metalloproteinase (MMP)-cleavable crosslinker with exposure to different concentrations of collagenase.

Consistent with the degradation kinetics, encapsulated proteins, such as VEGF, can be released with controlled rates, which may be determined using enzyme-linked immunosorbent assay (ELISA). In one embodiment, more than 90% of VEGF is encapsulated within the capsules (FIGS. 6 and 7). FIG. 3C shows a graph illustrating various concentrations of VEGF released from nVEGF prepared with different percentages of degradable crosslinkers with and without the presence of plasmin. In the absence of plasmin, no free VEGF is detected in any nVEGF sample, demonstrating that no VEGF is released and that VEGF antibody could not bind to nVEGF. In the presence of plasmin, nVEGF degradation leads to the release of the encapsulated VEGF. The amount of VEGF released systematically increases with an increasing percentage of degradable crosslinker used during the nanocapsule synthesis, indicating that the rate of VEGF release can be modulated effectively. It is worth pointing out that in one illustrative embodiment, nVEGF formed with 100% degradable crosslinker released 95% of the VEGF used to form the nanocapsules, indicating that VEGF can be effectively encapsulated and released using this technology.

This method can be generalized for protein delivery not only with rate control but also with specificity to the enzyme present. To demonstrate this concept, nBSA containing plasmin-cleavable crosslinker KNRVK (SEQ ID NO: 1) (denoted as $nBSA_{NRV}$) or MMP-cleavable crosslinker KLGPAK (Lys-Leu-Gly-Pro-Ala-Lys) (SEQ ID NO: 4) (denoted as $nBSA_{LGPA}$) is used in an illustrative embodiment. Plasmin, a serine protease in blood, is commonly secreted by tissue cells during the formation of vessels, while MMP plays an important role in tissue remodeling to degrade extracellular matrix proteins during angiogenesis (see, e.g. M. S. Pepper, *Arterioscier., Thromb., Vasc. Biol.* 2001, 21, 1104; Y. Okada, et al. *Pathol. Int* 2010, 60, 477). FIG. 3D shows an illustrative SDS-PAGE image of native BSA, $nBSA_{NRV}$, and $nBSA_{LGPA}$ without and with exposure to plasmin or collagenase (a bacterial equivalent of MMP, capable of degrading MMP sensitive peptides) for 30 min (see, e.g. D. J. Harrington, *Infect. Immun.* 1996, 64, 1885). Compared to the characteristic band of native BSA (line 1), $nBSA_{NRV}$ without exposure to plasmin (line 2) or after exposure to collagenase (line 4) does not show any well-defined band, but does exhibit a well-defined band (line 3) similar to that of native BSA upon exposure to plasmin. This observation clearly demonstrates that the release of BSA is highly specific to the enzyme exposed and confirms a feasibility to deliver protein with enzyme specificity. Similarly, exposing $nBSA_{LGPA}$ to plasmin (line 5) results in broad dispersion in the gel, confirming that plasmin is incapable of triggering release of BSA from MMP-specific $nBSA_{LGPA}$. Exposing $nBSA_{LGPA}$ to collagenase results in specific degradation of the polymer shells, which is confirmed by DLS study (FIG. 7). This demonstrates that the specific enzyme-degradation of nanocapsules can be achieved by making judicious choice of enzymes and particular peptide crosslinkers with specific sequences.

Figure 4:
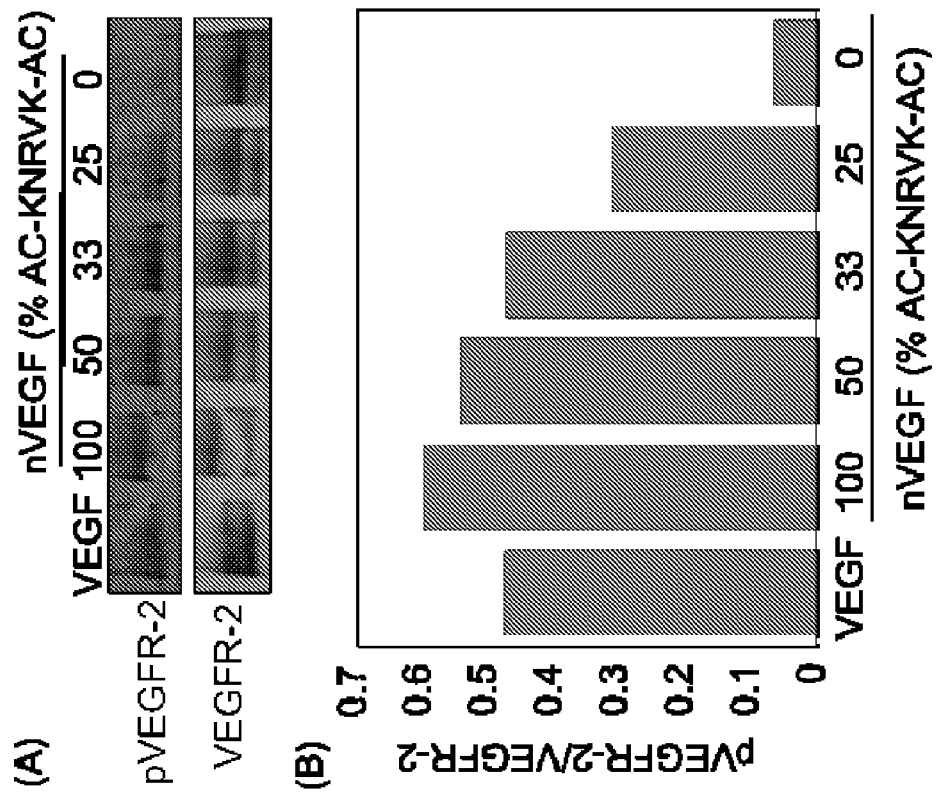

In another illustrative embodiment, to demonstrate the bioactivity of the encapsulated proteins, the ability of released VEGF to phosphorylate its receptor was assessed and compared with native VEGF. In this example, VEGF nanocapsules with different percentages of the plasmin degradable crosslinkers (100% to 0%) were exposed to plasmin for 15 min. and added to confluent HUVECs for another 5 min. A western blot of the exposed cells was run and probed for phosphorylated VEGFR-2 as well as the total VEGFR-2 (FIG. 4A). Clearly, all nVEGF that contained the degradable crosslinker showed receptor phosphorylation, indicating that the VEGF released from the nanocapsules was active. Further, these data show that the nanocapsules were degraded to a sufficient extent by plasmin to release their VEGF cargoes. Care was taken to expose the cells to the same amount of VEGF for all the conditions. FIG. 4B shows a histogram of normalized pVEGFR-2-band intensities versus that of total VEGFR-2 for each sample ($I_{pVEGFR-2}/I_{VEGFR-2}$). Native VEGF and the 100% degradable nVEGF show a similar level of receptor phosphorylation, indicating that the nanocapsules well preserve the VEGF activity. Further, nVEGF prepared without the plasmin degradable crosslinker (0%) shows a ratio less than 0.1, confirming the degradation of the nanocapsules is required for receptor phosphorylation. This demonstrates the ability to controllably release proteins, such as growth factors, from the nanocapsules.

Figure 5:
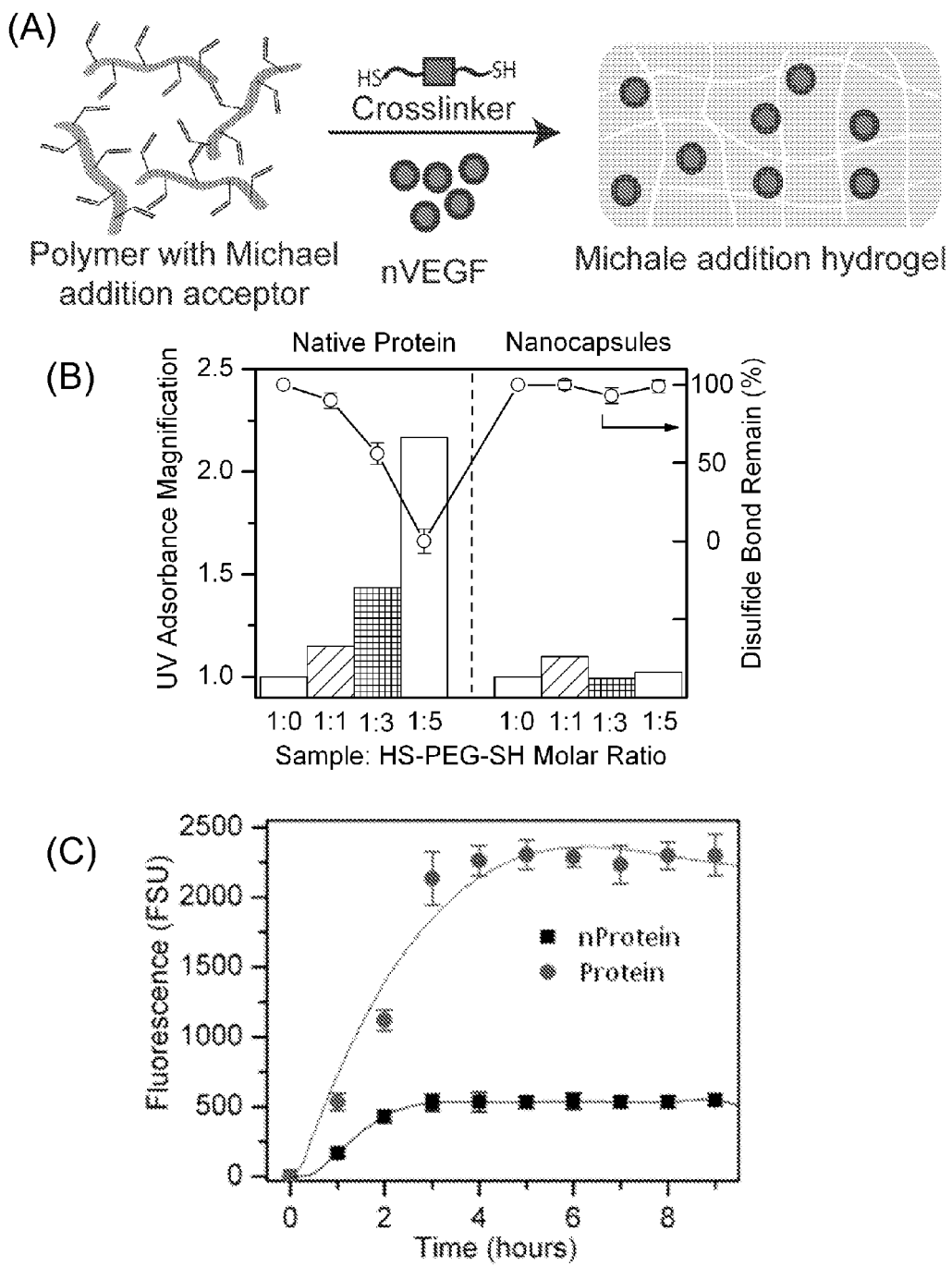

Such protein nanocapsules with highly retained activity, controlled released capability, and specificity are of great interest for a broad range of applications ranging from therapeutics to tissue engineering. In certain embodiments of the invention, polymeric nanocapsules are disposed within a three dimensional matrix comprising a hydrogel. For example, as illustrated in FIG. 5A, hydrogel scaffolds are commonly synthesized by reacting a polymer containing vinyl groups with crosslinkers containing dithiol groups, during which Michael addition reaction between the vinyl and thio groups effectively crosslinks the polymer into a hydrogel (see, e.g. T. Segura, et al. *Biomaterials* 2011, 32, 39). Proteins including growth factors can be directly added to the mixture of the polymer and crosslinker and incorporated within the hydrogels (see, e.g. K. Ladewig, *Expert Opin. Drug Delivery* 2011; A. J. Garcia, et al. *Proc. Natl. Acad. Sci. USA* 2010, 107, 3323; M. R. Lutolf, et al. *Nat. Biotechnol.* 2003, 21, 513). Although such hydrogels are extensively used for tissue regeneration applications, the crosslinkers may react with disulfide bridges of the proteins, resulting in structural misfolding and loss of activity. Since the nanocapsules contain the protective shells that prevent the encapsulated protein from reacting with the crosslinkers, the nanocapsules can be effectively incorporated within the hydrogel with better-retained activity.

Rapid leaching of the incorporated proteins from hydrogels has been a challenge that is required to be addressed (see, e.g. P. K. Shireman, et al. *J. Vasc. Surg.* 1999, 29, 852). One may consider decreasing the pore size of the hydrogels to decrease or avoid leaching of incorporated proteins. Nevertheless, to ensure cellular growth and nutrient diffusion into the hydrogels from surrounding media, hydrogels with large enough pore size are often required, which inevitably causes leaching of the incorporated protein. Fortunately, in certain embodiments of the invention, the protein nanocapsules described here generally contain residual vinyl groups on their surface, which can be immobilized to the hydrogel network through the Michael addition reaction with the thio-containing crosslinkers. Such an immobilization process effectively prevents leaching of the nanocapsules. In one illustrative embodiment, fluorescence-labeled BSA and BSA nanocapsules were incorporated within HA hydrogels, which were then placed in PBS buffer for different amounts of time. FIG. 5C compares the fluorescent intensities of the BSA or nBSA leached into the buffer solution. Clearly, fluorescent intensity of the leached BSA rapidly increased with time, which is much higher than that of the leached nBSA. This demonstrates that using protein nanocapsules rather than native proteins can effectively reduce leaching of the protein from the hydrogels.

To demonstrate the enhanced stability of the encapsulated proteins, in one illustrative embodiment, VEGF, native VEGF, and nVEGF were incubated with crosslinker HS—$(CH_2CH_2O)_{75}$—SH (HS-PEG-SH) for 30 min, allowing an exchange reaction between the disulfide bonds within the VEGF with the thiol groups of the crosslinker molecules. Such an exchange reaction results in an increasing number of thiol groups within the VEGF, which can be quantified using the Ellman's test. In a typical assay, generated thiol groups are reacted with 5,5'-dithio-bis(2-nitrobenzoic acid) (DTNB) and stoichiometricly release 2-nitro-5-thiobenzoate ions with a characteristic absorbance at 412 nm. FIG. 5B compares the relative absorbance intensity after incubating native VEGF and nVEGF (made with 100% degradable crosslinker) with different amounts of HS-PEG-SH for 30 min followed by addition of DTNB. For the native VEGF, the absorbance increases systematically with an increasing amount of HS-PEG-SH used, showing an increasing degree of reaction between the VEGF disulfide bonds with the crosslinker molecules. The disulfide bonds surviving the reaction rapidly decrease; at VEGF:HS-PEG-SH molar ratio of 1:5, all the disulfide bonds were broken. In contrast, the absorbance for nVEGF remains constant and the disulfide bonds were retained at all nVEGF:HS-PEG-SH ratios, demonstrating that the encapsulated VEGF is immune from the crosslinker attack. This demonstrates that encapsulating proteins within the nanocapsules can effectively prevent such inactivating reactions, providing a novel approach for the design and fabrication of regenerative bio-scaffolds.

As noted above embodiments of the invention include compositions of matter comprising at least one polypeptide, and a polymeric network linked by a plurality of crosslinking moieties having different material properties. As used herein, the term "polymeric network" or alternatively "polymeric shell" refers to one or more polymers interconnected within and/or between each other to form a mesh or shell. In typical embodiments of the invention, the polymeric network is coupled together by peptide bonds so as to form a shell that encapsulates the polypeptide. The polymeric shell forms a nanocapsule that inhibits the ability of the polypeptide contained within it to contact agents (e.g. enzymes, substrates and the like) outside of the shell. In typical embodiments, the peptide bonds are disposed within this polymeric network in an orientation designed so that they can be proteolytically cleaved when exposed to selected proteases within an external environment, and the cleavage of these bonds alters the shell in a manner that allows the polypeptide to migrate from the shell into the external environment. As is known in the art, a peptide bond (amide bond) is a covalent chemical bond formed between two molecules when the carboxyl group of one molecule reacts with the amino group of the other molecule. Peptide bonds occur between amino acids, and polypeptides and proteins are chains of amino acids held together by peptide bonds. Typically in such embodiments, the polypeptide is entrapped within, but not coupled to the polymeric network. In alternative embodiments, the polymer network is coupled to the polypeptide(s) at, collectively, at least 1, 2, 3, 4, 5, 7, 10, 15, or 20 locations.

A variety of monomers can be used to form polymeric networks useful in embodiments of the invention. A monomer unit is a chemical moiety that polymerizes, forming the polymer network of the nanocapsule. In some embodiments, monomer units comprise a polymerizable group having double bond, such as a vinyl, acryl, acrylamido, alkylacryl, alkylacrylamido, methacryl or methacrylamido group. Optionally different monomers are used. The polymerizable group of the different monomer units may be the same or different, so long as they are capable of forming a co-polymer under the conditions used to form the nanocapsule. For example, vinyl and acryl groups may form co-polymers under free-radical polymerization conditions.

In general, any number of different monomer units may be used to form polymers with the polypeptides, so long as the different monomer units are all capable of forming a polymer under the conditions used to form the nanocapsule. Monomer units with different side-chains may be used to alter the surface features of the nanocapsule (e.g. surface charge). The surface features may be controlled by adjusting the ratio between different monomer units. In some embodiments, the monomers may be neutral, uncharged, hydrophilic, hydrophobic, positively charged, or negatively charged. In some embodiments, the polymer network as a whole is neutral, uncharged, hydrophilic, hydrophobic, positively charged, or negatively charged. Solubility of the nanocapsule may be adjusted, for example, by varying the ratio between charged and uncharged, or hydrophilic or hydrophobic monomer units. In some embodiments, the nanocapsule has a positive or negative charge.

In some embodiments, at least one monomer unit has a positive or negative charge at the physiological pH (~7.4). By using monomer units having a charge at pH=7.4, the overall charge of the nanocapsule may be varied and adjusted by changing the ratio of the charged and uncharged monomer units. In some embodiments, the monomer unit has a positive charge at pH=7.4. Using positively charged monomer units enables the formation of nanocapsules having a positive charge. The charge may be adjusted by changing the ratio of neutral and positively charged monomer units.

Examples of specific monomer units and their functions include acrylamide (neutral, 1), 2-hydroxyethyl acrylate (neutral, 1), N-isopropylacrylamide (neutral, 2), sodium acrylate (negatively charged, 3), 2-acryloylamido-2-methylpropanesulfonic sodium (negatively charged, 3), allyl amine (positively charged, 4), N-(3-aminopropyl) methacrylamide hydrochloride (positively charged, 4, 5), dimethylamino ethyl methacrylate (positively charged, 5), (3-acrylamidopropyl) trimethylammonium hydrochloride (positively charged, 5), methyl acrylate (hydrophobic, 6) and styrene (hydrophobic 6). The numbers in the parentheses refer to functions: 1 to 5: hydrophilic surface and moisture retention; 2) temperature responsive; 3) negatively charged surface; 4) reactive sidechain for surface modification, 5) positive charge surface, 6) hydrophobic surface.

In embodiments of the invention, the polymer network further includes at least two types of crosslinking agents. In typical embodiments, at least one crosslinker used to form the polymeric shell is a crosslinker that includes a peptide and/or forms peptide bonds that links portions of the polymeric shell. In such crosslinkers, the peptide includes an amino acid sequence that is cleaved by a protease, for example one know to occur in an environment in which the polypeptide is being delivered. Optionally for example, the amino acid sequence that is cleaved by the protease comprises KNRVK (SEQ ID NO: 1) (e.g. is cleaved by plasmin), GGIPVSLRSGGK (SEQ ID NO: 2) (e.g. is cleaved by MMP-2), GGVPLSLYSGGK (SEQ ID NO: 3) (e.g is cleaved by MMP-9), or LVPRGS (SEQ ID NO: 5) (e.g. is cleaved by thrombin). In typical embodiments of the invention, the amino acids in the linker are L-amino acids. In certain embodiments of the invention, the amino acids in the linker are D-amino acids. For example, one can form nanocapsules with 100% D-amino acid peptides. In working examples using crosslinking agents comprising D-amino acid peptides that are cleaved by plasmin, ELISA studies confirmed the release of VEGF from nanocapsules upon plasmin treatment.

While motifs recognized by proteases such as plasmin and matrix metalloproteinases (e.g. MMP-1. MMP-2, MMP-3, MMP-7, MMP-9, MMP-13, MMP-14 etc.) are identified as illustrative sequences for use in the nanocapsule linkers of the invention, a wide variety of protease recognition motifs can be used in embodiments of the invention. Descriptions of illustrative protease recognition motifs that are capable of being specifically recognized and cleaved by a protease can be found, for example, in *Proteases: Structure and Function* by Klaudia Brix and Walter Stöcker (SPRINGER, 2012); *The Cancer Degradome: Proteases and Cancer Biology* by Dylan Edwards, Gunilla Hoyer-Hansen, Francesco Blasi and B. F. Sloane (Springer, 2008); *Proteases of Infectious Agents* by Ben M. Dunn (Academic Press, 1999). Moreover, Fischer et al. describes 280 motifs which are recognized by caspases (Fischer U., et al. *Cell Death Differ.* 2003, 10(1):76-100). A description of Presenilins, BACE and Alzheimer disease-related proteases can be found in Hooper N M, et al. *Biochem Soc Trans.* 2000, 28(4):441-6. A description of Proprotein and prohormone convertases can be found in Seidah N G, et al. *Brain Res.* 1999, 848(1-2):45-62. A description of proteases responsible for pathogen activation can be found in Kido, H et al., *Mol. Cells,* 1999, 9(3):235-44. See also, Tonello F, et al. *Adv. Exp. Med. Biol.,* 1996, 389:251-60; and Pettit S C, et al. *J. Virol.,* 2004, 78(16): 8477-85.

In certain embodiments of the invention, the protease is a naturally occurring human protease such as a matrix metalloproteinase, a thrombin, a plasmin, a mapsin, a caspase or the like. Embodiments of the invention can be adapted for use with proteases that are observed to be overexpressed in one or more human cancer cell lineages such as a cathepsin cysteine protease, a urokinase-type plasminogen activator, a collagenase, a stromelysin-1 or the like. Alternatively, the protease is not normally expressed in humans. For example, viral proteases, such as HSV proteases, CMV proteases, HBV proteases, HCV proteases, HIV-1 proteases, or other non-naturally occurring proteases (for that particular cell or organism) can used in embodiments of the invention. Proteases that recognize defined sequences of at least 4, or at least 5 or about 6 amino acid residues, can be used in different embodiments of the invention.

The size of the proteolytically degradable nanocapsules may vary depending on the size and number of polypeptides in the nanocapsule and the characteristics of the polymer network. In some embodiments, the nanocapsule comprising the polypeptide and the polymeric network is from about 5 nm to about 2000 nm in length as measured along its longest axis. In some embodiments, the length of the nanocapsule is at least about 10 nm, 20 nm, 30 nm, 40 nm, 50 nm, 60 nm, 70 nm, 80 nm, 90 nm, 100 nm, 125 nm, 150 nm, 175 nm, 200 nm, 250 nm, 300 nm, 400 nm, or 500 nm. In some embodiment, the length of the nanocapsule is no more than about 50 nm, 60 nm, 70 nm, 80 nm, 90 nm, 100 nm, 125 nm, 150 nm, 175 nm, 200 nm, 250 nm, 300 nm, 400 nm, 500 nm, 600 nm, 700 nm, 800 nm, 900 nm, 1000 nm, 1500 nm or 2000 nm. The nanocapsule can be of any shape, depending on the size, shape and number of the enzymes in the complex. In one embodiment, the nanocapsule is substantially round. In another embodiment, the nanocapsule is substantial oval, spherical, cylinder, or pyramid-like.

In certain embodiments of the invention, the polymeric network is designed to exhibit a specific material profile, for example one that facilitates the crossing of cell membranes. For example, in some embodiments of the invention, a polymeric network is formed from materials selected so that the nanocapsule exhibits a positive charge at pH 6, 7 or 8. In some embodiments of the invention, polymeric network exhibits a surface charge of between 3 and 5 millivolts in an extracellular milieu in vivo or in vitro. In common embodiments of the invention, the polypeptide comprises a native protein, for example one that stimulates cellular growth (e.g. VEGF). In certain embodiments of the invention, the shell can encapsulate two or more different polypeptides. In some embodiments of the invention, the polypeptide comprises a detectable marker (e.g. a green fluorescent protein).

Polymerization can be carried out according to art accepted practices used with the selected mixture components. In some embodiments, the polymerization is carried out at room temperature, though the temperature may be increased or decreased as desired, depending on the polymerization method, so long as the function of the polypeptide is not lost during polymerization. Where degradable crosslinkers or linking groups are used, the function of the nanoparticle may be measured after degradation of the polymer coating. Reaction temperatures may be increased where the polymerization reaction occurs too slowly, or where elevated temperature is needed to initiate polymerization. Temperatures may be decreased where polymerization reactions occur too quickly.

In some embodiments, the polymerization reaction is performed in water, or aqueous buffer. Other solvents may be used as desired, so long as the solvent does not interfere with the polymerization reaction, or degrade the desired polypeptide function. Mixtures of water or aqueous buffer and organic co-solvents may also be used, if necessary to dissolve reaction components, so long as the solvent mixture does not interfere with the reaction, or damage proteins such as enzymes and the like. In some embodiments, the polymerization reaction is performed in buffer.

In some embodiments, the method of producing a nanocapsule further includes a step of modifying the surface of the nanocapsule. Sidechains of the monomer unit(s) can be present on the surface of the nanocapsule after polymerization. Monomer units having a reactive sidechain (or protected reactive sidechain) may be used to prepare the nanocapsule. The reactive sidechain does not interfere with polymerization, but may undergo further chemical modification after the nanocapsule is formed (i.e. after polymerization is completed). A protected reactive sidechain may be deprotected using standard chemical deprotection methods, then reacted with a chemical modifying agent. A reactive sidechain is treated with a chemical reagent to covalently attach the surface modifying agent to the surface of the nanocapsule. The surface modification may be a small molecule, polymer, peptide, polypeptide, protein, oligonucleotide, polysaccharide, or antibody. The surface modification may alter the solubility of the nanocapsule (e.g. by adding polyethylene glycols or other hydrophilic groups), change the surface charge of the nanocapsule (e.g. by adding charged surface modifiers), or impart an additional function to the nanocapsule, such as light-emission, cell targeting or cell penetration. Examples of small molecule surface modifications include light emitting compounds, such as fluorescein, or rhodamine, or cell targeting compounds such as folic acid. Peptides and polypeptides may be used for cell targeting, and may include antibodies selective to specific cell surface features, cell signaling peptides, or hormones. Other peptides may be used to increase cell penetration of the nanocapsule (such as TAT or antennepedia homeodomain). In some embodiments, the surface modification is an antibody. Because nanocapsule can have an easily derivatized surface, specific antibodies can be conjugated with nanocapsules, providing enhanced targeted delivery.

The nanocapsules comprising a polymer network and a polypeptide as discussed herein can be formulated into various compositions, for use in diagnostic or therapeutic treatment methods. The compositions (e.g. pharmaceutical compositions) can be assembled as a kit. Generally, a pharmaceutical composition of the invention comprises an effective amount (e.g., a pharmaceutically effective amount) of a composition of the invention. Embodiments of the invention include kits useful for any of the methods disclosed herein, either in vitro or in vivo. Such kits can comprise one or more of the compositions of the invention. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form.

From the foregoing description, it will be apparent that variations and modifications may be made to the invention described herein to adopt it to various usages and conditions. Such embodiments are also within the scope of the following claims. The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof. Terms listed in single tense also include multiple unless the context indicates otherwise.

Methods for preparing, characterizing and using the nanocomplexes of this disclosure are further illustrated in the following Examples. Starting materials are made according to procedures known in the art or as illustrated herein. The following Examples are provided so that the invention might be more fully understood. These Examples are illustrative only and should not be construed as limiting the invention in any way.

The illustrative embodiments and examples disclosed herein are provided to illustrate the invention but not to limit its scope. Other variants of the invention will be readily apparent to one of ordinary skill in the art and are encompassed by the appended claims. All publications, databases, and patents cited herein (e.g. U.S. Pat. No. 6,153,217; U.S. Patent Application Publication No. 20090060894; International Application Number PCT/US2012/33515 filed Apr. 13, 2012 for: REDOX RESPONSIVE POLYMERIC NANOCAPSULES FOR PROTEIN DELIVERY; Wen, J. et al. *Advanced Materials*, 2011, 23(39), 4549-53) are hereby incorporated by reference for all purposes.

EXAMPLES

Now, the present invention will be described in detail in reference to various illustrative examples, but is not to be limited to these examples. As shown by the disclosure in the Examples below, protein nanocapsules that can release the encapsulated proteins with controllable rate and specificity to specific enzyme are provided. Embodiments of the invention provide new avenues of protein delivery that can be controlled by specific cellular events or local environments, which are of great importance for therapeutic and other applications. Furthermore, the unique nanocapsule structures protect the encapsulated proteins with robustness against the reaction system, enabling the synthesis of a series of hydrogel scaffolds for broad regenerative tissue applications. Though the disclosure mainly discusses the incorporation of BSA and VEGF, those of skill in the art will understand that a wide variety of other proteins may also be used. Consequently, the protease degradable nanocapsules may include other different protein cores and may be added to cells in culture that express the desired protease for release or be delivered in vivo, where the protein would be released only at sites where the protease is active.

Example 1: Synthesis of Nanocapsules

Bovine serum albumin (BSA) (250 µg) was dissolved into 500 µL of 10 mM pH 8.5 sodium bicarbonate buffer. First, the positively charged monomer N-(3-aminopropyl) methacrylamide (APmTAAm), prepared in a 10 mg mL$^{-1}$ aqueous solution, was added into protein solution with stirring for 10 min at 4° C. Then the acrylamide (AAm) monomer and crosslinkers (combination of bisacryloylated Lys-Asn-Arg-Val-Lys (KNRVK, SEQ ID NO: 1) peptide and N,N'-methylene bisacrylamide (BIS)) were added to the protein solution with stirring sequentially. The molar ratio of AAm:APM:crosslinker was adjusted to 5:5:1. Radical polymerization was initiated by adding both ammonium persulfate (1:10 molar ratio of total monomers) dissolved in deionized water and the same volume of 10% N,N,N',N'-tetramethylethylenediamine into the reaction solution. The size and zeta potential of nanocapsules were tuned by adjusting the ratios of protein to monomers used. The polymerization was allowed to proceed for 90-120 min in a nitrogen atmosphere at 4° C. Finally, unreacted monomers, crosslinker, and initiators were removed by dialysis in 10 mM pH 7.4 phosphate buffer. Synthesis of growth factor, vascular endothelial growth factor (VEGF), nanocapsules was similar to that of BSA nanocapsules. A ten times higher amount of monomer was required when the reaction volume was smaller than 50 µL and final protein concentration was lower than 0.05 µg µL$^{-1}$.

TABLE A

Illustrative syntheses using different initiator concentrations.

| [Initiators](µM) | | Number Mean Diameter | Polydispersity Index |
|---|---|---|---|
| 0.1 | #1 | 4.418 | 0.933 |
| | #2 | 5.311 | 1 |
| | #3 | 203.2 | 1 |
| 1 | #1 | 166.8 | 0.957 |
| | #2 | 183 | 0.888 |
| | #3 | 292.2 | 1 |
| 10 | #1 | 91.22 | 0.645 |
| | #2 | 68.49 | 0.677 |
| | #3 | 43.39 | 0.685 |
| 125 | #1 | 87.52 | 0.268 |
| | #2 | 43.02 | 0.313 |
| | #3 | 80.98 | 0.253 |
| 250 | | 92.8 | 0.232 |

Example 2: Materials and Methods for Preparing Protein Nanocapsules

Material.

All chemicals were purchased from Sigma-Aldrich unless otherwise noted, and were used as received. N-(3-Aminopropyl) methacrylamide was purchased from Polymer Science, Inc. Peptides KNRVK (SEQ ID NO: 1), KLGPAK (SEQ ID NO: 4) and GCREGPQGIWGQERCG (SEQ ID NO: 5) were purchased from NEOMPS (Genescript, Piscataway, N.J.). Vascular endothelial growth factor (VEGF) was a gift from Prof. Lonnie Shea's laboratory (Northwestern University). Sodium hyaluronan (HA) was a gift from Genzyme Corporation (60 kDa MW, Cambridge, Mass.).

Instruments.

UV-Visible adsorption was acquired with a GeneSys 6 spectrometer (Thermo Scientific). TEM images were obtained on a Philips EM-120 TEM instrument at 100000×. Zeta potential and particle size distribution were measured with a Malvern particle sizer Nano-ZS. Gross pictures of choriallantoic membrane (CAM) was recorded with Stemi 2000-C, Zeiss before the 1 mL FITC-dextran (0.5 mg/mL in PBS) was injected into the embryo. Fluorescent images of CAM with hydrogel were obtained with Zeiss Axio Observer Z1 fluorescence microscope. Fluorescent intensity of protein-containing solution was determined with Turner 9200-002 P2 biosystems instrument. Lyophilized samples were obtained by using a Labconco, Freezone 6 Plus freeze-dryer.

Peptide Crosslinker Modification.

A peptide crosslinker was obtained by reaction between the amine groups of the peptide and N-acryloxysuccinimide-PEG-biotin at 1:2 molar ratio at pH 7.4 for 2 hours at room temperature. The resulting solution was dialyzed overnight against DI $H_2O$ to remove unreacted substrates, lyophilized overnight and stored at −20° C. (see, e.g. Takalian, T. Shrum, C. T.; Kadoya, W. M.; Segura, T. *Biomaterials* 2010, 31, 8072-8080).

Characterization of Protein Nanocapsules.

The hydrodynamic size distribution and Zeta Potential of protein nanocapsules were measured by a dynamic light scattering (DLS, Malvern particle sizer Nano-ZS). After protein nanocapsules were negatively stained by 1% phosphotungstic acid (PTA) solution for TEM observation.

Release of Protein.

SDS-PAGE analysis was conducted before and after 30 min cleavage treatment. Released growth factor from the nanocapsules after 30 min enzyme treatment was detected by enzyme-linked immunosorbent assay (ELISA) (see, e.g. Anderson, S. M., et al. *Biomaterials* 2009, 30, 4618-4628). Briefly, 100 µL/well of mouse anti-human VEGF (Capture Antibody, 100 ng/mL) in PBS was used to coat a 96-well microplate. After incubated overnight at room temperature and blocked by adding 300 µL 1% BSA in pH=7.2 PBS for 1 hour at room temperature. 400 µL 0.05% Tween 20 pH 7.2 PBS was filled in each well to wash before and after blocking After three washes, 100 µL of sample (0.01 pM/mL) was added per well and incubated for 2 hours at room temperature. Before and after 100 µL of biotinylated goat anti-human VEGF (100 ng/mL) was added per well and incubated 2 hours at room temperature, three washes were done. 100 µL of streptavidin conjugated horseradish peroxidase was successively added and incubated for 20 min at room temperature, followed by washing three times. The substrate 1:1 mixture of Color Reagent A ($H_2O_2$) and Color Reagent B (Tetramethylbenzidine) was added (100 µL/well), and the plate was incubated for 20 min at room temperature avoiding direct light. The reaction was stopped by 50 µL of 2 N $H_2SO_4$ and determined by using a plate reader (BioTek PowerWave XS, Winooski, Vt.) at 570 nm absorbance. An approximate concentration of the naked VEGF can be estimated based on the standard absorbance intensity-concentration line.

Example 3: Hydrogels with Protein Nanocapsules

Preparation of Hydrogels with Protein Nanocapsules.

Acrylated hyaluronic acid (HA-AC) was prepared as previously described by a two-step synthesis (see, e.g. Lei, Y., et al. *J. Control. Release* 2011, doi:10.1016/j.jconrel.2011.01.028). First, 1.0 g hyaluronic acid (HA) was reacted with 18.0 g adipic dihydrazide (ADH) at pH 4.75 to prepare HA-ADH in the presence of 2.0 g 1-ethyl-3-[3-dimethylaminopropyl] carbodiimide hydrochloride (EDC) overnight and purified through dialysis (8000 MWCO) in DI water for one week. Secondly, 1.0 g HA-ADH was reacted with 0.75 g N-acryloxysuccinimide in HEPES buffer (pH=7.2) overnight and purified through dialysis in DI water for 1 week. Hydrogels were formed by Michael Addition reaction between bis-cysteine containing MMP-labile peptide (Ac-GCRE-GPQGIWGQ-ERCG-$NH_2$ (SEQ ID NO: 6) crosslinker and HA-AC in 0.3 M TEOA buffer with nanocapsules. The gel precursor was glutinous and able to be placed between two Teflon plates. After incubated at 37° C. for 30 min, hydrogels with fluorescence-labeled samples were bathed in PBS in incubator to monitor the leaching; while hydrogels with functional VEGF were placed on the chick chorioallantoic membrane to induce vessel formation.

Activity of Released Protein.

A standard Western Blot procedure was used to probe surface-bound ability of released VEGF to phosphorylate VEGFR-2 (see, e.g. Chen, T. T., et al. *J. Cell Biol.* 2010, 188, 595-608). HUVECs are passed and seeded in 6-well plate the day before cell treatment. The cells were incubated in serum-free medium for 6 h and then incubated in 0.1 mM $Na_3VO_4$ for 5 min. 5 nM VEGF nanocapsules (nVEGFs) were treated by 0.2 mg/mL plasmin (in PBS) at room temperature for 15 min, then 200 ng VEGF (nVEGF) was added into cell medium and incubated for 5 min. Cells were removed from the plate by incubated in lysis buffer (1% Triton X-100, 10 mM Tris-HCl, 150 mM NaCl, 30 mM sodium pyrophosphate, 50 mM sodium fluoride, 2.1 mM sodium orthovanadate, 1 mM EDTA, 1 mM phenylmethylsulfonyl fluoride and 2 µg/mL aprotinin) at room temperature for 5 min. Cell lysate with the same amount of bicinchoninic acid was diluted in loading buffer (1 M Tris-HCl, 20% SDS and 50% glycerol, 5% (v/v) β-mercaptoethanol) separated by SDS-PAGE and transferred to nitrocellulose membranes under 400 mA voltage for 2 h. The membranes were blocked and bound to primary antibodies.

Released VEGFs were detected by chemical fluorescence with a Typhoon scanner after incubated with secondary antibodies coupled with horseradish peroxidase. Typhoon images were quantitatively analyzed by ImageJ software. Chick chorioallantoic membrane (CAM) testes were done by the condition described in previous literatures (see, e.g. Lobrinus, J. A.; Juillerat-Jeanneret, J.; Darekar; P.; Schlosshauer, B.; Janzer, R. C. *Dev. Brain Res.* 1992, 70, 207-211). Fertilized eggs (Hy line chicks, Atlanta Ga.) were fenestrated at 37° C. and 60% humidity and chorioallantoic membrane of 3 day was exposed in disks. The eggs were reincubated another 7 days and grafted hydrogels with native VEGF or nVEGF onto the membrane at day 10. For perfusion studies, 1 ml of FITC-dextran (500 µg/mL) was intravenous injected at a rate of 500 μL/min. Small incisions were made in the periphery to allow exsanguination. Following a 5-minute perfusion, pieces of membrane were fixed (4% formaldehyde, 4° C., 10 min.) and prepared for imaging in an epifluorescent stereomicroscope.

Stability of Nanocapsules in Hydrogel.

Protein and nanocapsules were respectively incubated with HS—(CH$_2$CH$_2$O)$_{75}$—SH (HS-PEG-SH, M$_w$=3400) at 37° C. for 30 min. After that, mixtures of the protein/nanocapsules and HS-PEG-SH were incubated at room temperature for 15 min with 5,5'-Dithio-bis(2-nitrobenzoic acid) (DTNB) (10:1 molar ratio to HS-PEG-SH). DTNB reacts with free thiols and releases out 2-nitro-5-thiobenzoate, which has a yellow color and can be measured by the absorbance of visible light at 412 nm with a GeneSys 6 spectrometer (Thermo Scientific) (see, e.g. Kuhn, S. J.; Finch, S. K.; Hallahan, D. E.; Giorgio, T. D. *Nano Lett.* 2006, 6(2), 306-312.). A calibration curve of SH concentration was constructed by tested absorbance at 412 nm after DTNB reacted with cysteine. Free thiol group amount was calibrated by comparing the UV/vis absorbance difference from the standard curve.

Release of BSA and nBSA from the Gels.

The hydrogel precursors were mixed with 3.5 pmol FITC-labeled BSA or nBSA and allowed to crosslink for 30 min at 37° C. After the gel formation, the hydrogels were cut to fit into 96-well plates and swelled in 400 μL PBS buffer in the incubator at 37° C. for different times. Leaching of the fluorescent-labeled proteins from the hydrogels was monitored by testing the fluorescence of PBS buffer on a Turner 9200-002 P2 biosystems instrument.

Example 4: In Vitro and In Vivo Validation of Protein Nanocapsules

This example demonstrates that (i) nGFs with controlled size and surface properties can be readily made, (ii) that nGF are more resistant to chemically induced inactivation than naked proteins, and (iii) that controlled and cell-triggered release of the protein cargo can be achieved with the use of protease degradable peptides as nanocapsule crosslinkers.

Plasmin Degradable nVEGF (De-nVEGF$_{plasmin}$) Synthesis and Characterization.

Plasmin degradable VEGF nanocapsules were synthesized using the proposed encapsulation approach, where a charged monomer is electrostatically bound to the protein surface and is used as the initiation site for radical polymerization (detailed methods below). The polymerization acrylate monomers were mixed in with some peptide crosslinkers that contain acrylates on either side of the peptide. This results in complete encapsulation of the protein within a nanosized hydrogel that is crosslinked by the peptide.

The size of the VEGF nanocapsules was characterized by TEM and DLS (FIG. 11). The nanocapsule size did not completely agree between the TEM and DLS. While TEM showed an average size of 25 nm, DLS showed an average size of 100 nm (FIG. 11). This could be explained by the hydration state of the particles. TEM is done with dried samples, while DLS is performed in hydrated swelled samples. Nevertheless, the particles appear uniform by both methods.

Detailed Method of Synthesis and Characterization.

GF (~10 μM) was mixed with the charged monomer, acrylamide, and crosslinker (molar ratio is 1:1500:1500:300, or 1:3000:3000:600) in 10 mM pH 8.5 sodium bicarbonate buffer in a total volume of 10 uL. The polymerization was initiated by adding 0.65 μL of 20 mg/mL ammonium persulfate and 0.58 μL N,N,N',N'-tetramethylethylenediamine to the resulting solution. The reaction was allowed to proceed for 1.5-hrs under $N_2$ on ice. Finally, dialysis at 4° C. against 10 mM pH 7.0 phosphate buffer was used to remove excess monomers and initiators. The ratio of peptide to bis-acrylamide crosslinker was varied from 1:0 to 0:1 in order to study the degradation rates possible.

de-nVEGF$_{plasmin}$ Activity.

To determine the activity of the released GFs, released GF were used to perform western blots (WB) for receptor phosphorylation. For WBs, human umbilical vein endothelial cells (HUVEC) were plated on 6-well plates and exposed to 100 ng/mL of released GF or fresh GF for 5 minutes. The cells were then lysed and processed using WB techniques (see, e.g. Anderson, S. M., et al. Biomaterials 30, 4618-4628 (2009); Chen, T. T. et al. The Journal of Cell Biology 188, 595-609). The intensity of the phosphorylated receptor bands were first normalized to the total receptor band and then compared between released GF and fresh GF. This comparison resulted in a percentage activity of the released GF.

With increasing amount of plasmin-degradable crosslinker used to composite the nanogel, more VEGF can be released after incubation with plasmin and be detected in ELISA, whereas VEGF encapsulated with 0% degradable-crosslinker has similar readings before and after plasmin treatment, indicating the complete and non-susceptible encapsulation of GF by the nanogel (FIG. 18). Also, the released VEGF retains its biological activity in being able to activate VEGFR-2 into phosphorylation, shown in WB experiment's data (FIGS. 4A and 13B). Quantitatively, 100%, 50% and 33% degradable crosslinker groups of nVEGF showed phosphorylation capability of their VEGFs, if released, comparable to that of an equivalent amount of native VEGF (FIGS. 4B and 13C), suggesting of little loss of VEGF bioactivity in the process of nanogel encapsulation.

Modulating De-nVEGF Degradation Rate.

The range of degradation rates were determined for two purposes: 1) with multiple peptide crosslinkers and different ratios of degradable to non-degradable crosslinkers to form the nGF, one sought to find the slow releasing and fast degrading nGF synthesis conditions. This would mean that one could deliver one single GF for an extended period of time or deliver multiple GF with different release kinetics so that one is activated early on during regeneration (1 to 7 days) and one is activated later on during regeneration (7 to 30 days). 2) For the single GF signal scenario, continuing presentation of GF can be achieved by the slow release from degradable nGF (de-nGF) in the presence of cell-secreted proteases. This would be beneficial towards stabilizing neovasculature, because even mature and stable vessels were shown to retract when the GF signal is consumed and short of availability (see, e.g. Ehrbar, M. et al. Biomaterials (2007)). Combinations of release kinetics and the presence of a single GF during the entire regeneration process may be the key for long lasting vessels.

nVEGF Degradation.

de-nVEGF$_{plasmin}$ (100%-peptide crosslinker) was incubated by itself, with plasmin (for certain amount of time according to its activity) and with trypsin (w:w=VEGF amount in de-nVEGF:trypsin=1:0.2) or collagenase IV (w:w=1:0.2) for 10, 20 30 minutes at 37° C. Equal molar of aprotinin was added to plasmin and trypsin treated nVEGF for another 5 min incubation to quench further digestion of freed VEGF by these enzymes. Samples were then diluted to 3 ng/mL before plating for ELISA according to the manufacturer's manual. Concentration of released VEGF was quantified by comparing to a standard curve in ELISA. Compared with the low amount of free VEGF in the no-protease-treated nVEGF (below 10%), plasmin-incubated nVEGF showed about 60% release percentage, whereas only extended periods of incubation with trypsin and collagenase IV had releases of VEGF (FIG. 19). Since trypsin is a generic protease that digests the peptide-crosslinker, as does plasmin, the degradation of nVEGF and release of VEGF through incubation of trypsin was expected; and the collagenase IV used was from a bacterial source and contained a low tryptic activity.

The degradation kinetics of nVEGF was quantified using DLS. In the presence of plasmin, the degradation profiles of nVEGFs prepared with different percentages of degradable crosslinkers were recorded by putting the hydrodynamic radius of nVEGF at time t, $R_t$, into the equation, % degradation=$[R_0-R_t]/[R_0-R_{VEGF}]$. As shown in FIG. 12C, nVEGF prepared with 100% degradable crosslinker was degraded completely after 40 min, while that prepared with 0% had no noticeable difference in size over time. And the slopes of the degradation profiles consistently increase with percentage of degradable crosslinkers, confirming of the controllable degradation rates by this GF encapsulation technique.

nVEGF Stability.

Dialyzed (against pH 7.0 phosphate buffer) nVEGF was stored in 4° C. and tested for the hydrodynamic size at different time points reported in FIG. 20 using dynamic light scattering. No aggregation of nVEGF was observed until the first 8 days, and continued measurements up to 3 weeks showed some aggregation by week 2 (FIGS. 2C and 20, respectively).

Example 5: Incorporation of Proteins into Hydrogels

This example demonstrates that (i) nGFs formed with four different GF cores can be incorporated into hydrogel scaffolds through the same approach regardless of the GF incorporated, (ii) that the encapsulated nGFs can activate co-encapsulated cells, and (iii) that hydrogels containing nGFs can induce angiogenesis in an in vivo angiogenesis assay.

There exists a critical need to develop strategies that can incorporate proteins into tissue engineering scaffolds without causing the inactivation of the GF. The ideal approach would utilize the same methodology for the incorporation of any GF. Current strategies to introduce GFs into synthetic hydrogels encapsulate naked GF into the hydrogel during gelation, covalently immobilize GF to the hydrogel precursors prior to gelation, or encapsulate GF into microspheres prior to gelation around the microspheres. However, these approaches result in the GF being exposed to the hydrogel crosslinking chemistry, the covalent modification of the growth factor or the exposure of the growth factor to the products of microsphere degradation (e.g. acidic environment), which results in degradation. Further, with the encapsulation approach GFs typically release quickly from hydrogel scaffolds (see, e.g. Zisch, A. H. et al. Faseb J 17, 2260-2262 (2003)) with no controlled release.

This example illustrates an innovative approach to introduce GFs into polyethylene glycol (PEG) hydrogels that are crosslinked with dicysteine containing peptides through Michael type addition. The approach involves the protection of the GF using a nanocapsule composed of a protease degradable hydrogel prior to its encapsulation inside the hydrogel. With this approach one can (i) achieve greater GF activity after PEG hydrogel formation, (ii) control the GF release rate and (iii) achieve cell mediated release of the GF.

De-nGF Protected from Intermolecular Disulfide Exchange with HS-PEG-SH.

The formation of Michael addition type of hydrogel takes place via the crosslink between the vinyl groups and thiol groups on the polymer and crosslinker. GFs can be incorporated into hydrogel by being mixed with precursors during the gelation process; however, thiol-containing crosslinkers may react with the intramolecular disulfide bridges within VEGF, resulting in protein misfolding and loss of activity. Here, it was found that nVEGF does not lose structural integrity as does naked VEGF after incubation with dithiol-containing crosslinker molecules.

Naked VEGF and nVEGF were incubated with varying molar equivalents of HS—$(CH_2CH_2O)_{75}$—SH (HS-PEG-SH) for 30 min, allowing inter-molecular disulfide exchange reaction between VEGF and the dithiol crosslinker molecule. Such exchange reaction in the excess of the additive dithiol molecule, if happened, would result in an increase in the number of thiol groups, which could be quantified in Ellman's assay by a further reaction with 5,5'-dithio-bis(2-nitrobenzoic acid) (DTNB) to stoichiometrically release 2-nitro-5-thiobenzoate ions with a characteristic absorbance at 412 nm.

For naked VEGF, the absorbance increases monotonically with the amount of HS-PEG-SH used, suggesting an increased degree of reaction between VEGF and the dithiol molecule. At VEGF:HS-PEG-SH molar ratio of 1:5, all the intramolecular disulfide bonds within VEGF were broken. On the other hand, nVEGF resists the exchange reaction by having no increase in the free thiol amount after incubation with HS-PEG-SH, indicating the protection of VEGF by the nanocapsule shell from the crosslinker attack. (FIG. 23)

De-nGF Loaded Hydrogel Release Rate.

Retaining incorporated GF inside hydrogels from leaching will greatly enhance the accessibility of encapsulated cells to GF within the matrix. While a small pore size may reduce the drainage of GF from hydrogel, it also limits the spreading and migration of encapsulated cells as well as the diffusion of nutrients from surrounding media. To address this issue, it was hypothesized that the residual vinyl groups on the nGF shell surface, as well as the enlarged size of nGF when compared to soluble GF, facilitate the immobilization of nGF in the hydrogel network through the Michael addition reaction with the thiol-containing crosslinker.

In the experiment, fluorescently-labeled BSA and nBSA were incorporated within hyaluronic acid hydrogels, which were then placed in PBS buffer for leaching over a period of 9 hours. Soluble BSA rapidly diffuses out of HA gel and increases the media fluorescent intensity by a great extent, while the leached intensity of nBSA was much lower. (FIG. 24)

Cell-Demanded Release of GF.

Since the de-nGFs are protease degradable, one expects that the de-nGF will be degraded through the action of cell released proteases. Similar to activity assay where released VEGF phosphorylates VEGFR-2 on HUVECs and such activation was measured with WB, HUVECs were incubated with de-nVEGF (100% degradable crosslinker) 50 ng/mL in PBS for a total of 2 hours to see if nVEGF can be degraded through cell-produced proteases. As a control, 50 ng/mL of native VEGF was used to treat HUVECs. Two pVEGFR/VEGFR activation-over-time profiles were normalized to have the highest intensity point of each trend be 1.

Seen in FIGS. 14 B and C, naked VEGF stimulates VEGFR-2 upon immediate interaction and such phosphorylation of VEGFR-2 lasts only for a short period of time, by 5 min, before saturation. However in the case of de-nVEGF, it sustains the phosphorylation activation of VEGF-receptor and such signal remains at the peak by 30 min. The extended amount of time with a high phosphorylation signal seen in HUVECs incubated with de-nVEGF demonstrates a prolonged interaction between nVEGF and HUVECs most likely due to the gradual release of the cargo VEGF by cell secreted proteases.

To further verify that the nanogel shell of nVEGF can be gradually degraded by cell secreted proteases to release VEGF, a consecutive cell incubation experiment was performed. De-nVEGF (50 ng/mL) was incubated with one set of HUVECs (n=3) for 30 min and then directly transferred to the next set of HUVECs for another 30 min. This process continued for a total of 4 sets of HUVECs and soluble VEGF (50 ng/mL) were treated with HUVECs the same way as controls. All the cell lysates were quantified with PathScan Phospho-VEGFR-2 (Tyr 1175) and Total VEGFR-2 Sandwich ELISAs, where absorbances at 450 nm of pVEGFR (1175) were normalized by that of total VEGFR.

The result (FIG. 21) showed that nVEGF strongly activates HUVECs in the 3rd time of cell contacts, with significant difference than soluble VEGF. This suggests that more VEGF is being released through the degradation of nVEGF by cell-produced proteases by the previous 3×30 min of cell contacts.

De-nVEGF$_{plasmin}$ Sustains the Sprouting of HUVECs within Fibrin Hydrogel.

Since nGF is well retained within hydrogel matrix (FIG. 24) and undergoes cell-demanded release of GF (FIGS. 14 and 21), it was hypothesized that cells embedded within a 3-D hydrogel matrix that has nGF incorporated can elicit the release of GF from retained nGF, which in turn induces biological responses of cells. To test the hypothesis, HUVEC sprouting assay was performed where early passages of HUVECs were pre-coated onto Cytodex beads before encapsulated into fibrin gel matrix for sprouting under different GF presentation conditions. This model mimics the process of angiogenesis seen in vivo, which provides a power tool for analyzing the interaction of GF and cells in this complex phenomenon. Previous researchers have shown that continuous addition of 2.5~5 ng/mL of VEGF yields the optimal HUVEC sprouting results (see, e.g. Nakatsu, M. N. et al. Microvasc Res 66, 102-112 (2003)), and the concentration of replenishing 2.5 ng/mL of VEGF was adopted as the positive control.

At day 4, sprouts became visible with nVEGF$_{200}$ and replenishing Vs$_{2.5}$. By day 8, tubes were significantly more under those two conditions than non-replenishing Vs$_{200}$. With only one initial addition of nVEGF, the core VEGF was slowly released to induce vessel formation as cells continuously degrade the nanocapsule shell. No repetitive supplementation of fresh VEGF was needed for tube formation and sprouting of HUVECs (FIGS. 15, 16, and 24).

Enhanced Angiogenesis In Vivo.

To further test the activity of the encapsulated nGF, the Chick Chorioallantoic Membrane (CAM) angiogenesis model was used as a rapid and efficient screen. It was expected that by using this model one could test the number of new blood vessels that are generated as a result of the signaling induced by the de-nGFs in comparison to the blank matrix.

White leghorn chicken hatched eggs were purchased from California Hatchery (CA) and incubated in a humidified chamber at 38° C. for 9 days. Egg shells were removed at day 3 and the embryos were transferred to a petri dish for continuing culture. Fibrin hydrogel, with a final concentration of 2 mg/mL of fibrinogen, was formed with the addition of thrombin, calcium, aprotinin and 1% penicillin/streptomycin. Acrylated hyaluronic acid were crosslinked with thiol-containing, MMP-sensitive crosslinker to have a final concentration of 3% w/v. To ensure sterility, HA-hydrogels were swollen in 1% penicillin/streptomycin for over 3 hours before implantation. At day 9 of incubation, hydrogels each of 30 μl were made containing 1 μg/mL nVEGF, 1 μg/mL VEGF and no protein cargo (blank gels), which were grafted onto the same CAM in areas avoiding the embryo and pre-existing major vessels. 2 days later, micrographs were captured on a small Zeiss microscope, and vessels were slowly perfused with 5 mg/mL of FITC-dextran (2,000,000 mol. wt., Sigma) before overnight fixation in 4% paraformaldehyde. Fluorescent images were taken on a Zeiss microscope with a 20× objective lens.

As seen in FIG. 22, nVEGF elicited many new, small blood vessels, all radially oriented from the implant towards its surroundings. That was similar to the reaction soluble VEGF induced on CAM. As a control, blank gels of fibrin and hyaluronic acid had bigger vessels, which had no particular orientation around them, not eliciting positive or irritating responses.

Activity in an In Vivo Wound Healing Model.

The model we used was a full-thickness dermal wound created with a 4 mm-diameter biopsy punch on the backskins of female BALB/c mice (19-23 g, 13 weeks) (two wounds per mouse). 25 μL each of fibrin gel (fibrinogen 10 mg/mL) only, with naked VEGF of 100 ng, and with nVEGF 100 ng was placed on the wound before a splint with a 6 mm-diameter hole covered under Tegaderm was sutured around the wound. Images of the wound were taken on day 0, 1, 3, 5, 7 with a JENOPTIC ProgRes CT3 camera on the Carl Zeiss Stemi 2000-C microscope. Photographic images were analyzed using the ImageJ software by tracing the wound margin with a fine-resolution computer mouse and calculating the area. The rate of wound closure was expressed as the ratio of the nonepithelialized/nonvascularized areas at each time point divided by the area of the original wound at day 0. The analysis was performed in a blinded fashion by a different research not aware of the treatment that each animal received. Considering a non-normal distribution, Kruskal-Wallis one-way analysis (post test of Dunns all pairs compared) was performed for statistical comparison. The results are given as mean±SD.

This concludes the description of the illustrative embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

The invention claimed is:

1. A composition of matter comprising:

at least one polypeptide;

a polymeric network, wherein:

polymers in the polymeric network are coupled together by a first crosslinking agent and a second crosslinking agent so as to form a shell that encapsulates the polypeptide;

the first crosslinking agent comprises a peptide having an amino acid sequence that is cleaved by a protease, wherein amino acid sequence that is cleaved by the protease comprises KNRVK (SEQ ID NO: 1), GGIPVSLRSGGK (SEQ ID NO: 2) or GGV-PLSLYSGGK (SEQ ID NO: 3); and the second crosslinking agent does not comprise a peptide having an amino acid sequence that is cleaved by a protease;

wherein the polymers, the first crosslinking agent and the second crosslinking agent are disposed within the polymeric network in an orientation so that proteolytic cleavage of the first crosslinking agent releases the polypeptide from the shell into an external environment.

2. The composition of claim 1, wherein relative molar amounts of the first crosslinking agent and the second crosslinking agent in the shell are at least 1:5, 1:4, 1:3, 1:2, 1:1, 2:1, 3:1, 4:1 or 5:1.

3. The composition of claim 1, wherein shell that encapsulates the polypeptide has a diameter between 15 and 35 nanometers.

4. The composition of claim 1, wherein the polypeptide comprises a protein that stimulates cellular growth.

5. The composition of claim 1, wherein the composition further comprises a hydrogel in which the shell is disposed.

6. The composition of claim 5, wherein the shell is covalently coupled to the hydrogel by a hydrogel crosslinking agent.

7. The composition of claim 6, wherein the hydrogel crosslinking agent comprises a peptide having an amino acid sequence that is cleaved by a protease.

8. The composition of claim 1, wherein the first crosslinking agent comprises a peptide having D-amino acids.

9. The composition of claim 1, wherein the concentration of the first crosslinking agent in the composition relative to the concentration of the second crosslinking agent in the composition is controlled so as to modulate the rate at which the polypeptide is released from the shell into an external in vivo environment.

10. The composition of claim 9, wherein the concentration of the first crosslinking agent is greater than the concentration of the second crosslinking agent in order to modulate the rate at which the polypeptide is released from the shell into an external in vivo environment.

11. The composition of claim 9, wherein the concentration of the first crosslinking agent is less than the concentration of the second crosslinking agent in order to modulate the rate at which the polypeptide is released from the shell into an external in vivo environment.

12. A composition of matter comprising:

at least two polypeptides;

a polymeric network, wherein:

polymers in the polymeric network are coupled together by a first crosslinking agent and a second crosslinking agent so as to form a shell that encapsulates the at least two polypeptides;

the first crosslinking agent comprises a peptide having an amino acid sequence that is cleaved by a protease, wherein amino acid sequence that is cleaved by the protease comprises KNRVK (SEQ ID NO: 1), GGIPVSLRSGGK (SEQ ID NO: 2) or GGV-PLSLYSGGK (SEQ ID NO: 3); and the second crosslinking agent does not comprise a peptide having an amino acid sequence that is cleaved by the protease;

wherein the polymers, the first crosslinking agent and the second crosslinking agent are disposed within the polymeric network in an orientation so that proteolytic cleavage of the first crosslinking agent releases the at least two polypeptides from the shell into an external environment.

* * * * *